(12) United States Patent
Feaster et al.

(10) Patent No.: US 6,746,850 B2
(45) Date of Patent: Jun. 8, 2004

(54) ASSAY FOR DETECTING, MEASURING AND MONITORING THE ACTIVITIES AND CONCENTRATIONS OF PROTEINS AND METHODS OF USE THEREOF

(75) Inventors: Shawn R. Feaster, Damascus, MD (US); Richard K. Gordon, Potomac, MD (US); Bhupendra P. Doctor, Potomac, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 35 days.

(21) Appl. No.: 09/848,370

(22) Filed: May 4, 2001

(65) Prior Publication Data

US 2002/0165620 A1 Nov. 7, 2002

Related U.S. Application Data

(60) Provisional application No. 60/202,201, filed on May 5, 2000.

(51) Int. Cl.⁷ .............................................. C12Q 1/46
(52) U.S. Cl. ....................................................... 435/20
(58) Field of Search .......................................... 435/20

(56) References Cited

U.S. PATENT DOCUMENTS 5,674,588 A * 10/1997 Porfido et al. ............... 435/7.1

OTHER PUBLICATIONS

Chemnitius et al., "Mipafox Differential Inhibition Assay for Heart Muscle Cholinesterases: Substrate Specificity and Inhibition of Three Isoenzymes by Physostigmine and Quinidine", Gen. Pharmacology 28 (4) : 565–75 (1997).*
Simeon–Rudolf et al., "Heterogeneity of human serum cholinesterase revealed by thiocholine substrates", Periodicum Biologorum 98 (3) : 331–5 (1996).*
Durrani et al., "Specific Inhibitors and Substrates Studies on the Cholinesterases of Fasciola Gigantica from Sheep and Goats", Cellular & Molecular Biology 29 (1) : 49–52 (1983).*
A. H. Anton, (1988) "Unexpected Cocaine–Induced Fatalities: A Possible Cause", Drug Intelligence Clinical Pharm, 22(11):914.
P. Devenyl, (1989) "Cocaine Complications and Pseudocholinesterase", Ann. Int. Med., 110:167.
P. Jatlow, (1979) "Cocaine And Succinylocholine Sensitivity: A New Caution", Anesth. Analg., 58(3);235–8.
C. E. Johanson, (1989) "The Pharmacology Of Cocaine Related To Its Abuse", Pharmacol Rev., 41(1):3–52.
M. Martinez–Abad, (1988) "Ranitidine–Induced Confusion With Concomitant Morphine", Drug Intelligence Clin Pharm., 22(11):914–5.
J. Massoulie, (1982) "The Molecular Forms of Cholinesterase and Acetylcholinesterase in Vertebrates", Annu Rev Neurosci., 4:47–106.
D. J. Stewart, (1979) "Cocaine Metabolism: Cocaine and Norcocaine Hydrolysis By Liver And Serum Esterases", Clin Pharmacol Ther., 25(4):464–8.
D. B. Weissman, (1983) "Prolonged Neuromuscular Blockade In A Parturient Associated With Succinylcholine", Anesth Analg., 62(4):444–6.
J. A. Wildsmith, (1972) "Serum Pseudocholinesterase, Pregnancy and Suxamethonium", Anaesthesia, 27(1):90–1.

* cited by examiner

*Primary Examiner*—Sandra E. Saucier
(74) *Attorney, Agent, or Firm*—Elizabeth Arwine

(57) ABSTRACT

An assay for detecting, measuring, or monitoring the activity or concentration of at least two proteins that have similar or overlapping properties is disclosed. The assay comprises first determining the sensitivity coefficients of the substrates for each of the proteins in which the concentrations are to be determined. This method may be used for detecting, measuring, or monitoring the activity and concentration of AChE, BChE, or both in a test sample which test sample may be whole and unprocessed blood or tissue. Also disclosed are methods of using the assay to detect a subject's exposure to an agent which affects cholinesterase, determine the efficacy or progress of a treatment, determine the amount of protection provided against exposure to an agent which affects cholinesterase, or both, screen a subject for having a drug sensitivity or a particular disease, detect a change in red blood cell count of a subject, determine whether a candidate compound affects cholinesterase. Also disclosed are devices and kits for detecting, measuring, or monitoring the activities and concentrations of AChE, BChE, or both.

15 Claims, 22 Drawing Sheets

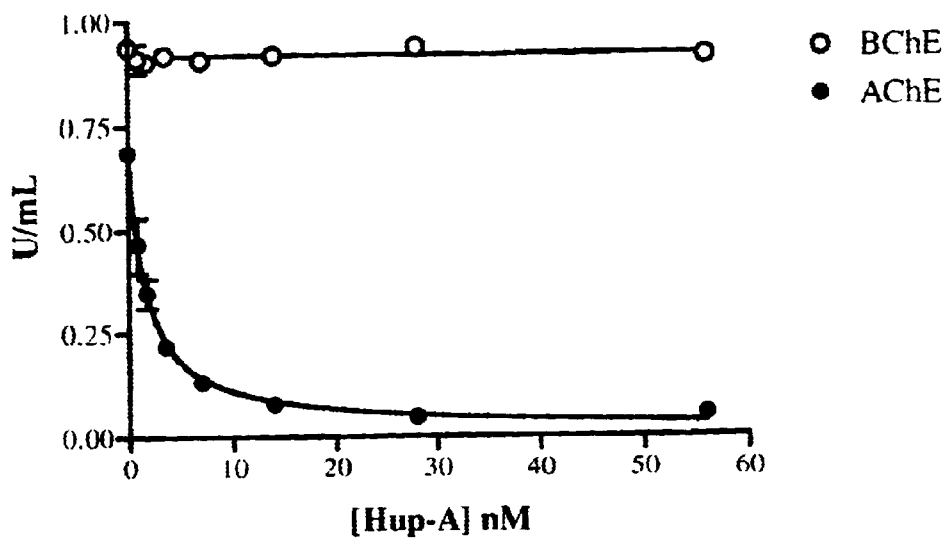
Figure 3A1
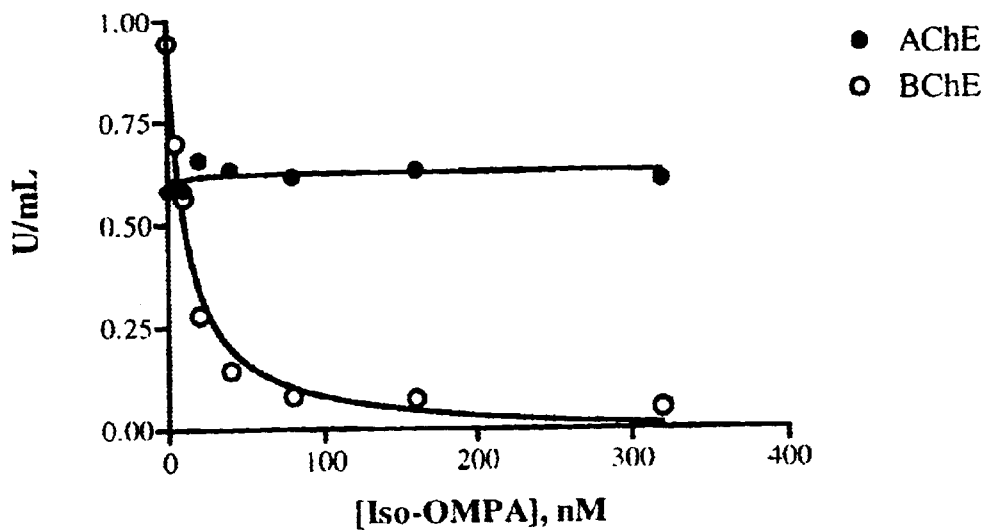
Figure 3B1

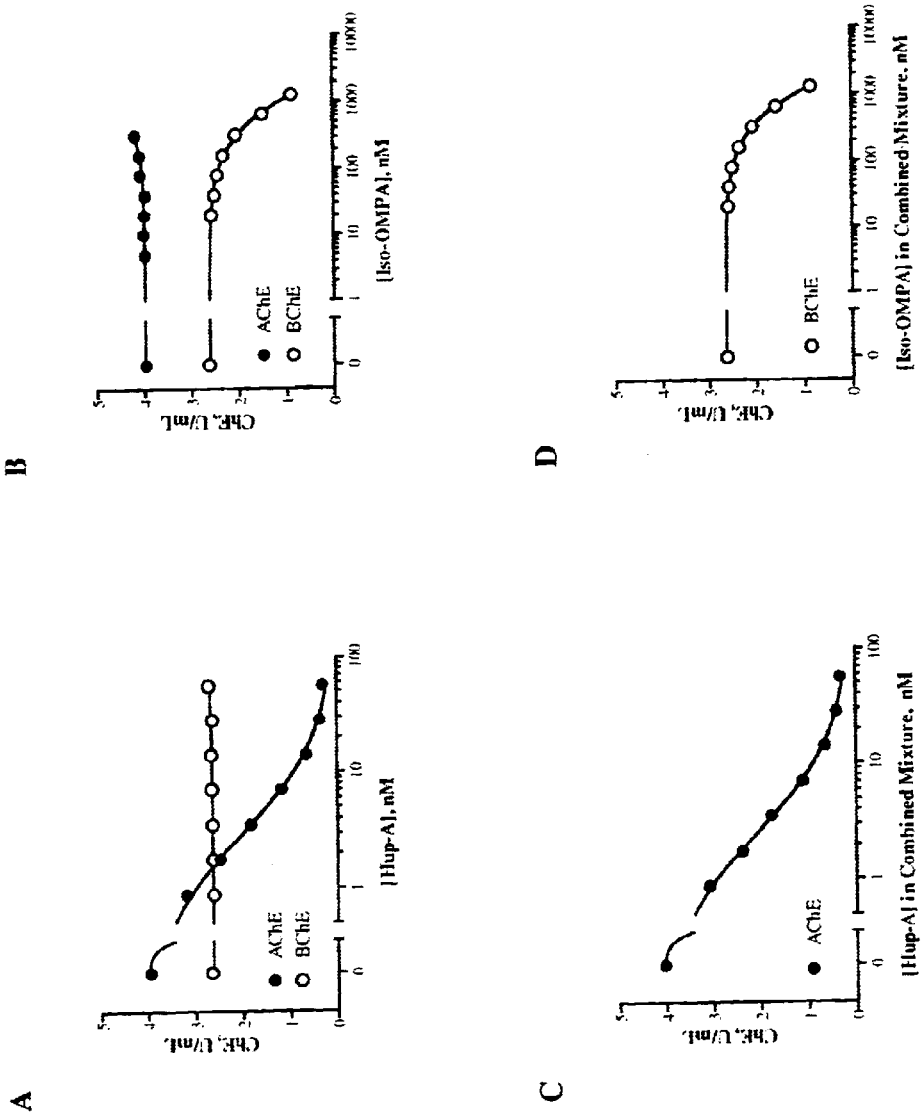
Figures 3A-D2

ASSAY FOR DETECTING, MEASURING AND MONITORING THE ACTIVITIES AND CONCENTRATIONS OF PROTEINS AND METHODS OF USE THEREOF

CROSS REFERENCE TO RELATED APPLICATIONS

This application claims the benefit of U.S. Provisional Patent Application No. 60/202,201, filed May 5, 2000, naming Shawn R. Feaster, Richard K. Gordon, and Bhupendra P. Doctor as inventors, which is herein incorporated by reference.

ACKNOWLEDGMENT OF GOVERNMENT INTEREST

This invention was made by employees and contractors of the United States Army. The government has rights in the invention.

BACKGROUND OF THE INVENTION

1. Field of the Invention.

The invention relates to an assay and a device for detecting and measuring the activities and concentrations of at least two proteins having similar properties or overlapping properties. In particular, the invention relates to an assay and a device for detecting and measuring the activities and concentrations of acetylcholinesterase (AChE), butyrylcholinesterase (BChE), or both in a sample.

2. Description of the Related Art.

Cholinesterases (ChEs) are highly polymorphic carboxylesterases of broad substrate specificity, involved in the termination of neurotransmission in cholinergic synapses and neuromuscular junctions. Some ChEs terminate the electrophysiological response to the neurotransmitter acetylcholine by rapidly degrading it, while the precise function of others is unknown. ChEs are classified into acetylcholinesterase (AChE) and butyrylcholinesterase (BChE) according to their substrate specificity and sensitivity to selective inhibitors. See Massoulie, J., et al., (1982) Ann. Rev. Neurosci. 5:57–106, which is incorporated herein by reference.

AChE is one of nature's most elegantly engineered proteins. AChE accelerates the hydrolysis of acetylcholine, a neurotransmitter, at nerve—nerve and neuromuscular junctions. BChE is found in mammalian blood, plasma, liver, pancreas, intestinal mucosa and the white matter of the central nervous system. BChE is also known as pseudocholinesterase and is sometimes referred to as serum cholinesterase as opposed to red blood cell cholinesterase, true cholinesterase, or AChE. BChE catalyzes the hydrolysis of a number of choline esters.

BChE also degrades cocaine ingested by a subject. Generally, cocaine is well tolerated by the majority of the population. However, acute cocaine abuse is related to a small incidence of sudden death. See Clouet, D. et al., Mechanisms of Cocaine Abuse and Toxicity, NIDA Research Monograph 88; and Johanson, C. and Fischman, M. W., (1989) Pharmacol. Rev. 41:3, which are both incorporated herein by reference. Although the physiological basis for sudden death due to acute cocaine abuse is not known, it is possible that abnormal BChE activity and amounts may contribute to a subject's sensitivity to cocaine. See Stewart, D. J. et al., (1979) Clin. Pharmacol. Ther. 25:464; Jatlow, P., (1979) Anesth. Anag., 58:235; Anton, A. H., (1988) Drug Intell. Clin. Pharm. 22:914; and Devenyl, P., (1989) Ann. Int. Med. 110:167, all of which are incorporated herein by reference.

BChE hydrolyzes and inactivates muscle relaxants such as succinylcholine and related anesthetics. About 5% of the population have an abnormal genotype for BChE, which results in a severe deficiency in BChE activity and amounts. When a subject having an abnormal genotype for BChE is administered succinylcholine for inducing general anesthesia prior to surgery, the subject may experience a prolonged apnea as compared to a subject having a normal genotype for BChE during which the subject is unable to breathe and must be artificially ventilated until the succinylcholine is degraded by secondary mechanisms. As this condition is a potentially life-threatening situation, a subject may be screened for abnormal BChE activity and amounts and then administered BChE before, during, or after general anesthesia. Clearly, it would be desirable to periodically measure the subject's amounts, activities, and sensitivities of BChE, AChE, or both.

Succinylcholine sensitivity may also result from an abnormal BChE concentration or activity caused by pregnancy, diseases such as liver disease and hepatitis, or medications. See Wildsmith, J. A. W., (1972) Anesthesia 27:90; Weissman, D. B., et al., (1983) J., Anesth. Analg. 62:444; Singh, D.C., et al., (1976) J. Ind. Med. Assoc. 66:49; and Foldes, F. F., Enzymes in Anesthesiology, (1978) Springer-Verlag, NY, all of which are herein incorporated by reference.

As succinylcholine and cocaine sensitivity and other diseases such as Alzheimer's disease, glaucoma, and myasthenia gravis or any other such disease may be treated by regulating the concentrations or activities of AChE, BChE, or both, it would be desirable to detect, measure and monitor the concentrations and activities of AChE and BChE.

Nerve agents, chemical warfare agents, organophosphates (OPs), pesticides, insecticides, and other such noxious chemicals exert their toxic effects by inhibiting AChE, BChE, or both. Plasma BChE and erythrocyte AChE provide some protection to synaptic AChE from these neurotoxins by scavenging free circulating AChE toxins, BChE toxins, or both prior to absorption into the central and peripheral nervous systems. Only the non-scavenged neurotoxins are capable of attacking synaptic AChE. Therefore, a subject's susceptibility to these neurotoxins may be determined by measuring the concentrations and activities of AChE and BChE in the subject. Additionally, exposure to these neurotoxins may be determined by measuring the concentration and activity of AChE, BChE, or both in a subject suspected of being exposed.

As the concentrations and activities of AChE and BChE are affected by certain disease states and exposure to nerve agents, chemical warfare agents, organophosphates (OPs), pesticides, insecticides, anesthetics, and cocaine, it would be desirable to use the concentrations or activities of AChE, BChE, or both, as indicators of a subject's (1) sensitivity to a drug or chemical, (2) exposure to a nerve agent, a chemical warfare agent, an organophosphate, a pesticide, or insecticide, or (3) disease state.

Unfortunately, the prior art methods for detecting and measuring the concentrations and activities of AChE and BChE are often problematic and inaccurate. Prior art methods have significant drawbacks which include wide statistical error, long clinical turn around times, lack of standardization, the inability to reliably compare results between laboratories, use invasive sampling techniques, are not approved by the United States Food and Drug Administration, use somewhat large blood volumes, and necessitate processing the samples prior to testing, or both. Prior art methods include assays commonly known as gasometric (manometric), Michel, micro-Michel, pH stat, Ellman, and micro-Ellman. These techniques analyze carbon dioxide formation, change in pH, chromophore formation, peroxidase activity, and ultraviolet (UV) absorption. These prior art methods normally determine either the amount of AChE or BChE, but not both simultaneously as red blood cells, plasma, or selective inhibitors are used to measure one or the other. Methods utilizing selective inhibition will not accurately account for samples exposed to certain chemical agents or oximes. Additionally, methods utilizing selective inhibition prevent the simultaneous analysis of AChE and BChE within the same sample, thereby doubling the analysis time and introducing potential errors.

Generally, methods based on gas analysis comprise using acetylcholine as a substrate, bringing acetic acid produced by the enzymatic action of ChE into contact with sodium bicarbonate, and quantitatively determining the carbon dioxide gas produced. This method is problematic as it is cumbersome and difficult to employ high-throughput screening of many samples. Additionally, use of acetylcholine as a substrate is disadvantageous because acetylcholine tends to undergo non-enzymatic hydrolysis and has no high substrate specificity. Furthermore, to achieve greater sensitivity, radioactive sodium bicarbonate has been used which generates regulated waste. This is environmentally unfriendly and increases the cost of the assay.

A pH meter method, like the gas analysis method, comprises using acetylcholine as a substrate, and measuring a pH change due to acetic acid produced by the enzymatic action of ChE by means of a pH meter. The pH meter method suffers from problems similar to the gas method, as well as requiring frequent standardization.

A pH-indicator calorimetric method, unlike the pH meter method, comprises using acetylcholine as a substrate, and measuring a pH change due to acetic acid produced by ChE in terms of the molecular absorbance of the indicator. Indicators utilized include phenol red, bromothymol blue, and m-nitrophenol. Although the pH-indicator calorimetric method may be used to analyze many samples, the reaction time is long, the pH is not kept constant, and the obtained values are not sufficiently reproducible at low and high values.

Assays based on thiocholine color formation utilize acetylthiocholine, butylthiocholine or the like as a substrate. The substrate yields thiocholine by the enzymatic reaction of ChE, which then reacts with 5,5'-dithiobis-2-nitrobenzoic acid (DTNB) to produce a yellow color which is measured by a colorimeter. Although the thiocholine method has a high sensitivity, comprises simple operations, and many samples may be analyzed, it is detrimentally affected by the yellow coloration of bilirubin and hemoglobin in whole blood and is unavoidably affected by compounds having a thiol group such as glutathione. Additionally, the substrate itself is somewhat unstable.

Coupled enzymatic methods utilize benzoylcholine, orthotoluoylcholine or the like as a substrate. These substrate yield betaine by choline oxidase. Then 4-aminoantipyrine is subjected to oxidative condensation with phenol or the like which produces hydrogen peroxide in the presence peroxidase to cause color production. The enzymatic method is problematic since phenol or 4-aminoantipyrine, which is used as the reagent for the color-producing system, competitively inhibits ChE, and the amount of these reagents is limited and sufficient color production is difficult. Additionally, the use of hydrogen peroxide is affected by the presence of bilirubin, reducing substances such as ascorbic acid, and choline. Furthermore, benzoylcholine undergoes non-enzymatic hydrolysis.

One UV method utilizes benzoylcholine as a substrate wherein the decrease in amount of the substrate caused by hydrolysis due to the enzymatic action of ChE at 240 nm is monitored. This UV method is problematic as interference by serum components generally occurs at 240 nm and benzoylcholine undergoes non-enzymatic hydrolysis and the reaction can not be carried out in the optimum pH range of ChE. Additionally, there is a large deviation of absorption coefficient with respect to wavelength.

Another UV method utilizes p-hydroxybenzoylcholine as the substrate wherein p-hydroxybenzoate hydroxylase is reacted with p-hydroxybenzoic acid and the decrease in absorbance caused by the oxidation of NADPH into NADP is monitored at 340 nm. This UV method is problematic as it utilizes NADPH, which is expensive, unstable, must be made frequently, and needs to be kept frozen.

As described above, these conventional methods for determining the ChE activities and concentrations are cumbersome employ reagents and techniques with inherent problems that detrimentally affect precision and accuracy, and are ill suited for high-throughput screening.

There exists a need for an assay and a device for the rapid, accurate and precise detection and measurement of the activity and concentration of at least two proteins, such as AChE and BChE, having similar or overlapping properties towards a plurality of substrates.

SUMMARY OF THE INVENTION

In some embodiments, the present invention relates to an assay for detecting, measuring or monitoring the activity or concentration of a protein in a test sample, wherein the protein belongs to a plurality of proteins and the plurality of proteins have similar or overlapping properties towards a plurality of substrates, comprising determining the activity or the concentration of the protein in the test sample with each sensitivity coefficient of each substrate for the protein.

In the embodiments of the invention, the test sample may be a synthetic sample or a natural sample. Natural samples include tissues, fluids, or membranes. Fluids may include blood, serum, lymph, cerebrospinal fluid, breast milk, interstitial or urine. Tissues may include diaphragm, brain, liver, muscle, and kidney.

The sensitivity coefficients are determined from a sensitivity coefficient sample by obtaining a plurality of inhibited dilutions of the sensitivity coefficient sample, wherein the plurality of inhibited dilutions comprise a plurality of concentrations of the protein which are partially to completely inhibited; exposing each inhibited dilution of the plurality of inhibited dilutions to each substrate; measuring the reaction rates between each uninhibited protein in each inhibited dilution and each substrate; calculating the relationships between the reaction rates of each uninhibited protein and each concentration of the sensitivity coefficient sample at infinite inhibitor concentration; and extracting each sensitivity coefficient for each protein from the calculated relationships.

In some embodiments, the plurality of proteins comprise acetylcholinesterase and butyrylcholinesterase. In some embodiments, the plurality of substrates comprise acetylcholine, acetylthiocholine, butyrylcholine, butyrylthiocholine, propionylcholine, and propionylthiocholine. In some embodiments, the inhibitor is huperzine-A, tetraisopropyl pyrophosphoramide, or a combination thereof.

In some embodiments, the invention relates to an assay for detecting, measuring or monitoring the activity or concentration of acetylcholinesterase, butyrylcholinesterase, or both in a test sample comprising determining the activity or the concentration of acetylcholinesterase, butyrylcholinesterase, or both in the test sample with the sensitivity coefficients of each substrate for acetylcholinesterase, butyrylcholinesterase, or both. The plurality of substrates may comprise acetylcholine, acetylthiocholine, butyrylcholine, butyrylthiocholine, propionylcholine, and propionylthiocholine. Preferably, the substrates are acetylthiocholine, butyrylthiocholine, and propionylthiocholine. In these embodiments, the sensitivity coefficients are determined from a sensitivity coefficient sample by obtaining a plurality of dilutions of at least one inhibitor which selectively inhibits either acetylcholinesterase or butyrylcholinesterase; obtaining a plurality of dilutions of the sensitivity coefficient sample; adding each dilution of the inhibitor to each dilution of the sensitivity coefficient sample to obtain a plurality of inhibited sensitivity coefficient samples; exposing each inhibited sensitivity coefficient sample to each substrate; measuring the reaction rates between acetylcholinesterase and each substrate; measuring the reaction rates between butyrylcholinesterase and each substrate; calculating the relationship between the reaction rates of acetylcholinesterase and each concentration of the sensitivity coefficient sample at infinite inhibitor concentration; calculating the relationships between the reaction rates of butyrylcholinesterase and each concentration of the sensitivity coefficient sample at infinite inhibitor concentration; and extracting each sensitivity coefficient of each substrate for acetylcholinesterase and butyrylcholinesterase from the calculated relationships. The inhibitor may be huperzine-A, tetraisopropyl pyrophosphoramide, or a combination thereof. The reaction rates may be measured by utilizing a chromogenic substrate and measuring the absorbance of the reactions.

In some embodiments, the test samples may include an agent which affects the concentration or activity of acetylcholinesterase, butyrylcholinesterase, or both. The agent may be removed from the test sample prior to measuring the reaction rates.

In some embodiments, the present invention relates to a method of detecting or confirming whether a subject was exposed to an agent which affects the concentration or activity of acetylcholinesterase, butyrylcholinesterase, or both comprising obtaining a test sample from the subject; measuring the reaction rates between acetylcholinesterase and a plurality of substrates; measuring the reaction rates between butyrylcholinesterase and the plurality of substrates; and calculating the activity or the concentration of acetylcholinesterase, butyrylcholinesterase, or both with sensitivity coefficients of each substrate for acetylcholinesterase and butyrylcholinesterase.

In some embodiments, the present invention relates to a method of determining the identity of an agent which affects the concentration or activity of acetylcholinesterase, butyrylcholinesterase, or both to which a subject was exposed comprising obtaining a test sample from the subject; measuring the reaction rates between acetylcholinesterase and a plurality of substrates; measuring the reaction rates between butyrylcholinesterase and the plurality of substrates; and calculating the activity or the concentration of acetylcholinesterase, butyrylcholinesterase, or both with sensitivity coefficients of each substrate for acetylcholinesterase and butyrylcholinesterase; and comparing the activities or the concentrations with a database of activity and concentration acetylcholinesterase and butyrylcholinesterase profiles for agents which affect the concentration or activity of acetylcholinesterase, butyrylcholinesterase, or both.

In some embodiments, the present invention relates to a method of determining the efficacy or monitoring the progress of a treatment regime, wherein a subject is administered a compound which affects the concentration or activity of acetylcholinesterase, butyrylcholinesterase, or both comprising obtaining a test sample from the subject; measuring the reaction rates between acetylcholinesterase and a plurality of substrates; measuring the reaction rates between butyrylcholinesterase and the plurality of substrates; and calculating the activity or the concentration of acetylcholinesterase, butyrylcholinesterase, or both with sensitivity coefficients of each substrate for acetylcholinesterase and butyrylcholinesterase; and monitoring the activities or the concentrations of acetylcholinesterase, butyrylcholinesterase, or both as a function of time of the treatment regime.

In some embodiments, the present invention relates to a method of determining whether a subject suffers from a drug sensitivity or a disease which affects the activities or the concentrations of acetylcholinesterase, butyrylcholinesterase, or both comprising obtaining a test sample from the subject; measuring the reaction rates between acetylcholinesterase and a plurality of substrates; measuring the reaction rates between butyrylcholinesterase and the plurality of substrates; and calculating the activity or the concentration of acetylcholinesterase, butyrylcholinesterase, or both with sensitivity coefficients of each substrate for acetylcholinesterase and butyrylcholinesterase; and comparing the activities or the concentrations with a database of activity and concentration acetylcholinesterase and butyrylcholinesterase profiles which are typical of individuals suffering from given drug sensitivities and individuals suffering from given diseases which affect the activities or the concentrations of acetylcholinesterase, butyrylcholinesterase, or both.

In some embodiments, the present invention relates to a method of measuring the concentration of red blood cells in a subject comprising obtaining a test sample from the subject; measuring the reaction rates between acetylcholinesterase and a plurality of substrates; measuring the reaction rates between butyrylcholinesterase and the plurality of substrates; and calculating the activity or the concentration of acetylcholinesterase, butyrylcholinesterase, or both with sensitivity coefficients of each substrate for acetylcholinesterase and butyrylcholinesterase; determining a relationship between standard concentrations of red blood cells and the activities or the concentrations of acetylcholinesterase, butyrylcholinesterase, or both; and using the relationship to calculate the concentration of red blood cells of the sample.

In some embodiments, the present invention relates to a method of screening for a candidate compound which affects the concentration or activity of acetylcholinesterase, butyrylcholinesterase, or both comprising obtaining a test sample; measuring the reaction rates between acetylcholinesterase and a plurality of substrates; measuring the reaction rates between butyrylcholinesterase and the plurality of substrates; and calculating the activity or the concentration of acetylcholinesterase, butyrylcholinesterase, or both with sensitivity coefficients of each substrate for acetylcholinesterase and butyrylcholinesterase; and determining whether the concentration or activity of acetylcholinesterase, butyrylcholinesterase, or both changes.

In some embodiments, the present invention relates to a device for detecting, measuring or monitoring the activities or concentrations of acetylcholinesterase, butyrylcholinesterase, or both in a test sample wherein the device measures the reaction rates between acetylcholinesterase and butyrylcholinesterase and at least two substrates; and calculates the activities or the concentrations of acetylcholinesterase, butyrylcholinesterase, or both with sensitivity coefficients of each substrate for acetylcholinesterase and butyrylcholinesterase. The device may further comprise a cartridge comprising the reagents, buffers, substrates and standards for measuring the reaction rates.

In some embodiments, the present invention relates to a kit for detecting, measuring or monitoring the activities or concentrations of acetylcholinesterase, butyrylcholinesterase, or both in a test sample comprising substrates for acetylcholinesterase and butyrylcholinesterase. The kit may further comprise a device for measuring the reaction rates between acetylcholinesterase and butyrylcholinesterase and the substrates, and calculating the activities or concentrations acetylcholinesterase and butyrylcholinesterase. The substrates for acetylcholinesterase and butyrylcholinesterase may include acetylthiocholine, butyrylthiocholine, and propionylthiocholine. The kit may also include a chromogenic substrate. The kit may also include directions.

In some embodiments, the present invention relates to a biosensor capable of detecting an agent which affects the concentration or activity of acetylcholinesterase, butyrylcholinesterase, or both wherein the comprises a known mixture of acetylcholinesterase and butyrylcholinesterase immobilized on a support and a sealed chamber containing the known mixture of acetylcholinesterase and butyrylcholinesterase.

In some embodiments, the present invention relates to a database of sensitivity coefficients for calculating the activities or the concentrations of acetylcholinesterase, butyrylcholinesterase, or both made by a method comprising obtaining a plurality of inhibited dilutions of a sensitivity coefficient sample, wherein the plurality of inhibited dilutions comprise a plurality of concentrations of either acetylcholinesterase or butyrylcholinesterase which is partially to completely inhibited; exposing each inhibited dilution of the plurality of inhibited dilutions to each substrate in a plurality of substrates for acetylcholinesterase and butyrylcholinesterase; measuring the reaction rates between acetylcholinesterase and each substrate; measuring the reaction rates between butyrylcholinesterase and each substrate; calculating the relationship between the reaction rates of acetylcholinesterase and each concentration of the sensitivity coefficient sample at infinite inhibitor concentration; calculating the relationships between the reaction rates of butyrylcholinesterase and each concentration of the sensitivity coefficient sample at infinite inhibitor concentration; and extracting each sensitivity coefficient of each substrate for acetylcholinesterase and butyrylcholinesterase from the calculated relationships.

DESCRIPTION OF THE DRAWINGS

This invention is further understood by reference to the drawings wherein:

FIG. 3A1 is a graph demonstrating an ex vivo titration of Hartley guinea pig blood AChE as a function of racemic Huperzine-A concentration.

FIG. 3B1 is a graph which shows the concentration of BChE in Hartley guinea pig blood as a function of titration with tetraisopropylphosphoramide (Iso-OPMA).

FIG. 3A2 is a graph demonstrating an ex vivo titration of human blood AChE as a function of racemic Huperzine-A (rac Hup-A) concentration.

FIG. 3B2 is a graph which shows the concentration of BChE in human blood as a function of titration with tetraisopropylphosphoramide (Iso-OPMA).

FIG. 3C2 is a graph demonstrating the ex vivo titration of human blood AChE with a mixture of rac Hup-A and Iso-OMPA, wherein the results have been plotted as a function of the rac Hup-A concentration.

FIG. 3D2 is a graph demonstrating the ex vivo titration of human blood BChE with a mixture of rac Hup-A and Iso-OMPA, wherein the results have been plotted as a function of the Iso-OMPA concentration.

DETAILED DESCRIPTION OF THE INVENTION

Figure 1:
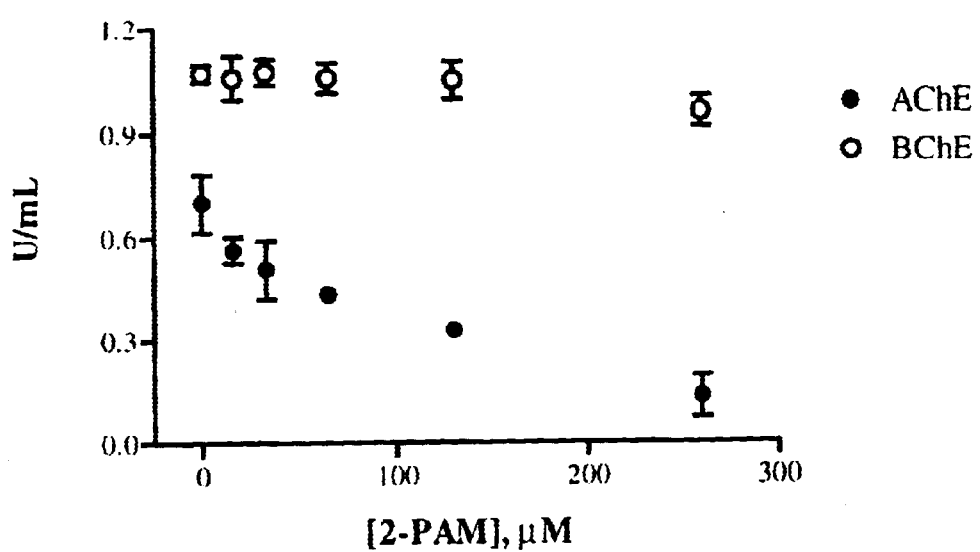
FIG. 1 is a graph which illustrates that AChE is inhibited by small concentrations of 2-PAM, an oxime and part of the United States Army's current treatment regime for organophosphate and pesticide poisoning, while BChE is relatively unaffected.

The present invention generally relates to an assay for detecting, measuring, or monitoring the activity or concentration of at least two proteins in a sample, which have similar or overlapping properties towards a plurality of substrates. As used herein, "similar or overlapping properties" means that the proteins react with the same plurality of substrates. For example, the proteins hydrolyze the same plurality of substrates. At a minimum, there should be one substrate for each protein. In preferred embodiments, the number of substrates used equals one substrate for each protein plus one. For example, if the concentrations or activities of two proteins, which have similar or overlapping properties, are to be determined, then at least three substrates are preferred. However, it is possible to conduct the assay with exactly the same number of substrates as proteins.

Generally, the present assay comprises first determining the sensitivity coefficients of the substrates for each of the proteins in which the concentrations are to be determined. The sample from which the sensitivity coefficients are to be determined will be hereinafter referred to as the "sensitivity coefficient sample" and the sample from which the activities or concentrations of the proteins are to be determined by using the sensitivity coefficients will be hereinafter referred to as the "test sample". Use of the terms "sample" or "samples" alone may refer to either the test or sensitivity coefficient sample or samples.

The sensitivity coefficients of the substrates for each of the proteins in which the concentrations are to be determined are specific for a given population, species or sample group. Therefore, if a test sample is obtained from a human subject, the sensitivity coefficients must be determined for humans. Likewise, if a test sample is obtained from a Sprague Dawley rat, the sensitivity coefficients must be determined for Sprague Dawley rats. Additionally, if a test sample is processed in a particular manner, the sensitivity coefficients should be determined with at least one sensitivity coefficient sample processed in the same or a substantially similar manner such that the test sample and the sensitivity coefficient sample do not have characteristics from each other which characteristics would affect how the proteins react with the substrates.

The sensitivity coefficient sample is preferably a pooled sample comprising a plurality of samples obtained from a plurality of representatives of the given population, species, or sample group. It is important to note that this assay may be applied to any test sample belonging to a given population, species or sample group so long as the sensitivity coefficients are determined from a sensitivity coefficient sample obtained from at least one representative of the given population, species or sample group.

It is also important to note that a first person may determine the sensitivity coefficients with a first pooled sample to measure the activities or concentrations of proteins in a test sample. A second person may determine the sensitivity coefficients with a second pooled sample and obtain sensitivity coefficients that are different from the first pooled sample. If the second person uses the sensitivity coefficients determined by the second pooled sample to measure the activities or concentrations of the proteins in the same test sample as the first person, the second person should obtain concentrations and activities that are the same as the first person's concentrations and activities.

Once the sensitivity coefficients are determined, the sensitivity coefficients need not be determined again for the given population, species or sample group. However, if the characteristics of the test sample differ significantly from the characteristics of the sensitivity coefficient sample, the sensitivity coefficients should be determined again from a sensitivity coefficient sample that has the same or substantially similar characteristics of the test sample to compensate for unforeseen complications due to non-routine sample processing.

Both the test sample and the sensitivity coefficient sample may be synthetic such as a mixture of chemical reagents and proteins or biological which includes tissues, biological fluids and membranes. However, if the test sample is a particular biological fluid, the sensitivity coefficient must be determined from a sensitivity coefficient sample of the particular biological fluid unless it is known that properties of the proteins remain unchanged irrespective of source (i.e., tissue, biological fluid, and membranes). The assay of the present invention may be applied to samples obtained from eukaryotes or prokaryotes. The assay may be applied to samples obtained from any organism.

The sensitivity coefficients are determined by optimizing the concentration range of the sensitivity coefficient sample, and adding various concentrations of an inhibitor selective for the proteins in which the concentrations are to be determined. At a minimum, there may be one less selective inhibitor per protein. For example, if the sensitivity coefficients are to be determined for two proteins, which have similar or overlapping properties, then at least one selective inhibitor is used.

The inhibitors are then added to several dilutions of the sensitivity coefficient sample. The inhibited diluted sensitivity coefficient samples are exposed to the substrates for the given proteins. Preferably, there should be one substrate for each protein plus one additional substrate, although having the same number of substrates as proteins is acceptable. For example, if the sensitivity coefficients are to be determined for two proteins, which have similar or overlapping properties, then three substrates for the proteins are preferably used. The substrates may or may not be specific for a given protein.

After the substrates are added, the rates or progression of the reactions between each protein and each substrate are simultaneously measured. The contribution of each protein to the reaction rate of each substrate is calculated as a function of the concentration of the sensitivity coefficient sample at an infinite inhibitor concentration. This calculation results in a linear relationship in which the sensitivity coefficients may be extracted from the calculated slopes. These sensitivity coefficients are then used to calculate the concentrations of the proteins in a test sample obtained from a subject belonging to the same population or species from which the sensitivity coefficients were determined.

Figure 10A:
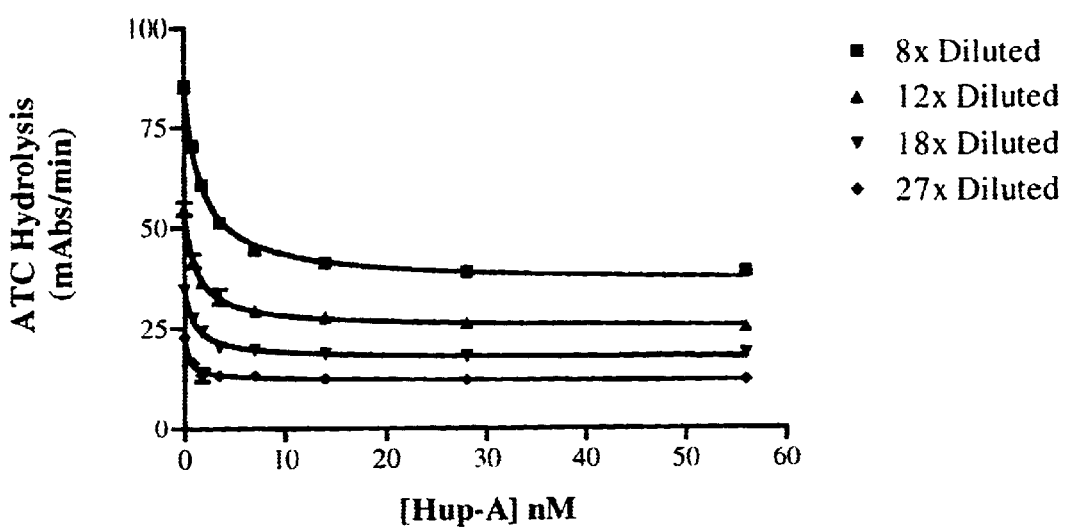
FIG. 10A is a graph showing the ex vivo titration of Hartley guinea pig blood with rac Hup-A at four dilutions of blood.
Figure 10B:
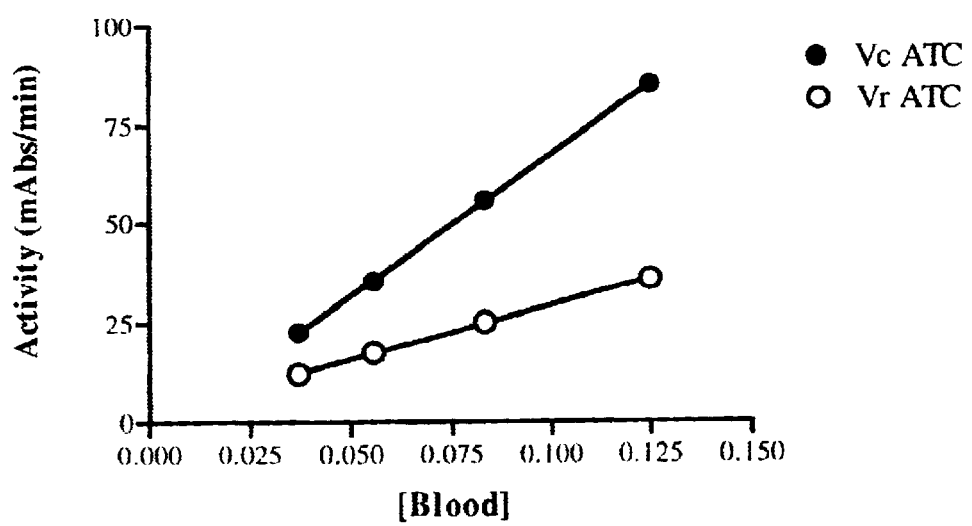
FIG. 10B is a replot of the parameters, Vc and Vr, obtained from the fits in FIG. 10A.

For example, FIG. 10A is a graph which shows the ex vivo titration of Hartley guinea pig blood with rac Hup-A at four dilutions of blood. The substrate used to monitor the extent of inhibition was acetylthiocholine (ATC). The data has been fit to the equation explained in Example 3 below. The fit parameters are used to generate the sensitivity coefficient data for AChE and BChE with respect to ATC. From this plot, the control activities (Vc) and residual activities (Vr) at infinite inhibitor concentration are obtained. FIG. 10B is a replot of the parameters, Vc and Vr, obtained from the fits in FIG. 10A. The slope of the Vr replot is the sensitivity coefficient for Hartley guinea pig blood BChE, and the difference in the slopes, i.e., slope Vc-slope Vr, is the sensitivity coefficient for AChE.

As an example, the present invention may be used to detect, measure, or monitor the activity and concentration of AChE, BChE, or both in a test sample. Generally, the assay for detecting, measuring, or monitoring the activity and concentration of AChE, BChE, or both in a test sample comprises first determining the sensitivity coefficient of an AChE substrate and the sensitivity coefficient of a BChE substrate. The assay for detecting, measuring, or monitoring the activity and concentration of AChE, BChE, or both in a blood sample provides greater than about 99% accuracy and less than about 1% precision in less than about five minutes. Again these sensitivity coefficients are specific for the test sample to be analyzed.

The sensitivity coefficients are determined by optimizing the concentration range of the sensitivity coefficient sample, and adding a selective AChE or a selective BChE inhibitor to several sensitivity coefficient sample dilutions. Suitable inhibitors include tetraisopropylphosphoramide (Iso-OMPA) (Sigma Chemical Co. MO), racemic huperzine-A (rac Hup-A) (CalBiochem-NovaBiochem Corporation, San Diego, Calif.), echothiophate (phospholine iodide) (Wyeth-Ayerst Laboratories, St. Davids, Pa.), ethopropazine, tacrine (Cognex) (Sigma, St. Louis, Mo.), E2020 (Aricept) (Eisai Inc. Teaneck, N.J.), edrophonium (Sigma, St. Louis, Mo.), or any other selective inhibitor for AChE or BChE known in the art. The inhibitors only need be selective over the concentration range used for the titration. Thus, suitable inhibitors may be selective inhibitors and need not be specific inhibitors. For example, if extremely high concentrations rather than nanomolar concentrations of Hup-A are used, BChE would also be titrated.

The inhibited sensitivity coefficient samples are then exposed to at least one AChE substrate, at least one BChE substrate and an additional substrate. None of these substrates needs to be specific for either protein. After the substrates are added, the catalytic rate of hydrolysis is measured either serially or simultaneously for all of the substrates. In preferred embodiments, the rates are measured simultaneously since the turnaround time is minimized, and temporal sample artifacts are minimized as in the case of transient or reversible inhibitors.

Next the contribution of AChE and BChE to the control sample is calculated as a function of the concentration of the sensitivity coefficient sample at an infinite inhibitor concentration. This is accomplished by plotting the residual activities at infinite inhibitor concentration as a function of sensitivity coefficient sample concentration for each substrate. The slopes from the resulting lines for each substrate are the sensitivity coefficients for the protein that was unaffected by the addition of the inhibitor. Furthermore, the sensitivity coefficients for the other protein are calculated by subtracting the aforementioned slopes from the corresponding control reactions for each substrate. See FIG. 10B. The sensitivity coefficients are then used to calculate the concentration of AChE and BChE in a test sample obtained from a subject belonging to the same population or species from which the sensitivity coefficient sample was obtained.

To confirm the sensitivity coefficients obtained by using a particular selective inhibitor of AChE or BChE, the method described above may be repeated by using a second selective inhibitor such as tetraisopropylphosphoramide (Iso-OMPA). Preferably the second inhibitor completely inhibits the other protein. Similar analysis of these rates as a function of serial dilution produces identical results.

It is noted, however, that use of only one inhibitor is sufficient. For example, if only Hup-A is used, the slope of rac Hup-A equals the sensitivity coefficient of BChE, and the slope of the control minus the slope of Hup-A equals the sensitivity coefficient for AChE. If only Iso-OMPA is used, the slope of the Iso-OMPA equals the sensitivity coefficient of AChE, and the slope of the control minus the slope of Iso-OMPA equals the sensitivity coefficient of BChE.

It is preferred that at least one of the substrates be of those normally used in clinical screening assays, since a wealth of information is available for these substrates. Suitable AChE substrates include acetylcholine and acetylthiocholine (ATC). Preferably, the AChE substrate is acetylthiolcholine. It is preferred that the BChE substrate be one normally used in clinical screening assays. Suitable BChE substrates include butyrylcholine, and butyrylthiocholine (BTC). Preferably, the BChE substrate is butyrythiolcholine. It is noted, however, that other suitable substrates include propionylthiolcholine (PTC), acetyl-$^{14}$C-choline, benzoylcholine, orthotoluoylcholine, p-hydroxybenzoylcholine, indophenyl acetate, indoxyl acetate, 2,6-dichloroindophenyl acetate, resorufin acetate or butyrate, other cholinesterase ester analogs, and other cholinesterase thioesters analogs may be used as a substrate by AChE, BChE, or both. A suitable substrate should possess specific AChE and BChE affinities, similar or overlapping AChE and BChE affinities, or both.

Figure 18:
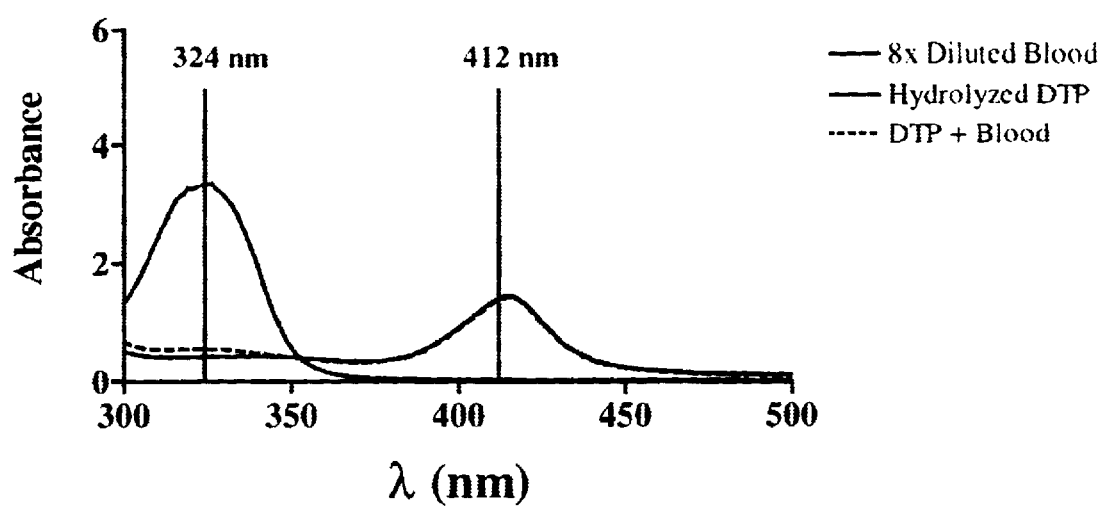
FIG. 18 depicts the peak resolution of 4-thiopyridine and that of the major hemoglobin band in Hartley guinea pig blood and further demonstrates that a mixture of 4,4'-dithiopyridine (the chromogenic substrate used in the assay of the present invention), does not significantly alter the blood sample.

Suitable chromogenic substrates include 5,5'-dithiol-bis (2-nitrobenzoic acid) (DTNB), 4,4'-dithiopyridine (DTP), disulfide analogs thereof, and 7-diethylamino-3-(4'-malemidylphenyl)-4-methyl courmarin (CPM). Preferably, the chromogenic substrate is DTP or a compound that does not have a maximum absorption at wavelengths that overlap with the absorbancies native to the sample. For example, DTP has a maximum absorbance at 324 nm and does not overlap with the absorbance range of about 375 nn to about 480 nm of hemoglobin in a whole blood sample. See e.g., FIG. 18. Thus, the absorbance of the whole blood sample at 415 nm, 445 nm, or any other wavelength between 375 nm and 480 nm may be used as a normalization marker for hemoglobin content in the sample. Thus, one may account for individual variations in red blood cell concentrations. Additionally, higher concentrations of blood may be used since blood does not absorb significantly in the region of 324 nm. Thus, the assay is no longer limited by instrumentation.

Both the test sample and the sensitivity coefficient sample may be synthetic such as a mixture of chemical reagents and proteins or natural which includes tissues, fluids and membranes. The samples may be processed or, more important unlike other conventional assays, unprocessed. The samples may be obtained from any subject or source in which AChE, BChE, or both are expected to be present. The fluids may be biological fluids which include blood, serum, lymph, interstitial, cerebrospinal fluid, breast milk, urine or any other fluid containing AChE, BChE, or both. Preferably, if the samples are blood, the samples are treated with any suitable anticoagulant known in the art. Preferred anticoagulants do not affect the concentrations and activities of AChE and BChE. Finger prick blood samples and intravenous blood samples produce the same or substantially similar results, thereby allowing relatively non-invasive blood sampling. The tissues include diaphragm, brain, liver, muscle, kidney, heart, lung, intestine, adrenal, or any other tissues possessing AChE, BChE, or both.

This procedure may be applied to tissues, and has been done successfully for Hartley guinea pig diaphragm. To prepare a tissue sample, the tissue is thoroughly homogenized using standard techniques known in the art. There is no need to separate the tissue from the supernatant, since excellent results were obtained by using the whole homogenate. In fact, the whole homogenate is a better representation of the sample than just the extract.

Figure 11:
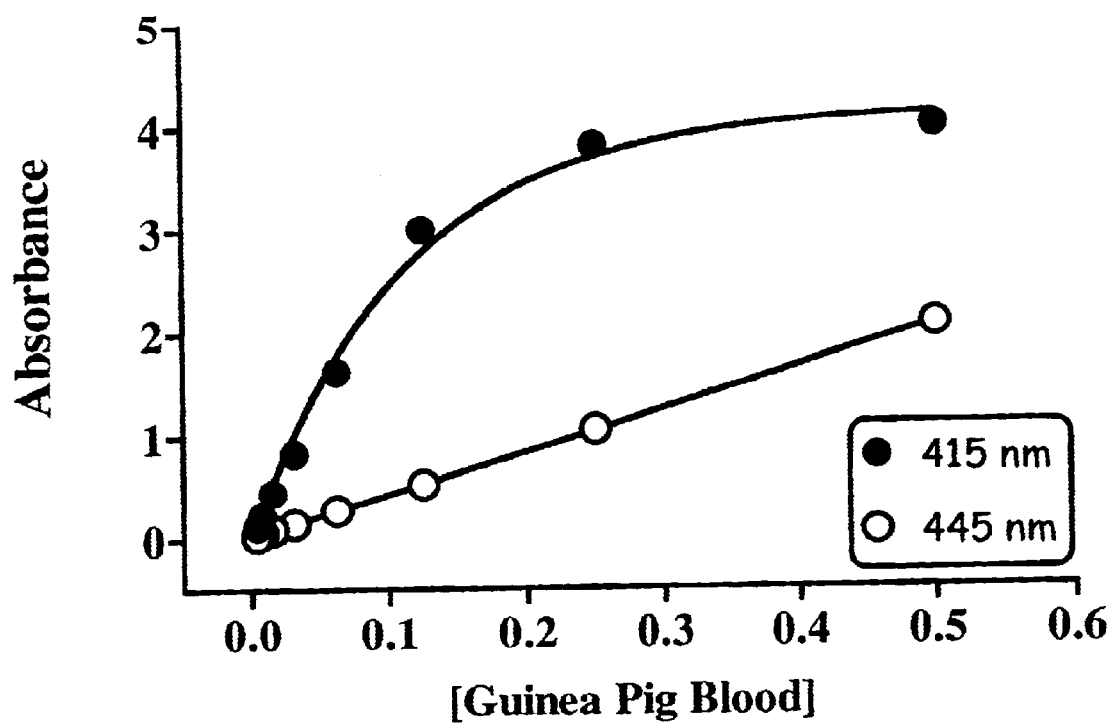
FIG. 11 is a plot which shows the absorbancy of Hartley guinea pig blood as a function of blood dilution at 415 and 445 nm.

The sensitivity coefficient sample range is optimized using a wavelength and concentration that provides a linear relationship between the sensitivity coefficient sample concentration and absorbance. For example, FIG. 11 is a plot which shows the absorbancy of Hartley guinea pig blood as a function of blood dilution at 415 and 445 nm. FIG. 11 demonstrates that a linear response of absorbance as a function of blood concentration may be obtained by using a hyperchromic shift from the peak maximum of hemoglobin.

For a blood or tissue sensitivity coefficient sample, the preferred range of absorbance is highly dependent on the analytical instrument. For example, using a the Molecular Devices SpectraMax Plus microplate reader (Molecular Devices Corporation, Sunnyvale, Calif.) a linear range of measurements can be achieved from approximately 0.01 to 4.0 absorbance units from about 200 nm to about 1000 nm. This allows blood dilutions from about 8 to 5000 fold to be used. On other instruments, however, the range may be only 0.01 to 1.0, necessitating a significantly smaller working range. One of ordinary skill in the art may determine by standard techniques the preferred range for the particular analytical instrument used.

Next, sensitivity coefficients are determined for several dilutions of the sensitivity coefficient sample optimized by sample and population normalization. See e.g., FIGS. 10A, 10B, and 11. The practical dilution range for human whole blood samples is from about 600 to 4000. Then the sensitivity coefficients are used to calculate the concentration or activity of AChE, BChE, or both in a test sample.

The assay of the present invention may be used to determine or confirm exposure to an agent that affects the concentration or activity of AChE, BChE, or both. For example, the assay may be used to analyze a test sample obtained from a subject to determine if or confirm that the subject was assaulted with a nerve agent. The assay may be used to confirm suspected cholinesterase poisoning due to organophosphates, organophosphites, carbamates, or the like. The assay may also be used to determine whether a subject was exposed to a particular agent as a particular agent may affect cholinesterase concentrations in a manner that may be distinguishable from the cholinesterase concentrations caused by other agents. Once exposure is determined or confirmed, an appropriate containment, decontamination, treatment or a combination thereof may be initiated.

The assay of the present invention may also be used to determine the efficacy or progress of a treatment wherein a compound which affects the AChE, BChE, or both is administered to a subject suffering from an abnormal concentration or activity of AChE, BChE, or both. By monitoring the ChE content as a function of time of the treatment, one may determine the effect the treatment has on the concentration or activity of AChE, BChE, or both and, if desired, modify the treatment to have the desired affect.

The assay may be used to monitor the concentration or activity of AChE, BChE, or both in a subject exposed to a compound which affects the concentration or activity of AChE, BChE, or both. In particular, the simultaneously monitoring the AChE and BChE concentrations or activities of a test sample can provide early detection of compounds which affect the concentration or activity of AChE, BChE, or both such as nerve agents, chemical warfare agents, organophosphates (OPs), pesticides, and insecticides. Since AChE and BChE have different affinities for particular compounds, it is possible to determine which compound or type of compound is present.

To accomplish this, an activity and concentration profile for each possible compound would be established. The profile would indicate how a given compound affects the activities and concentrations of AChE and BChE as a function of time and compound concentration. Then first responders would be able to confirm exposure to a nerve agent, a chemical warfare agent, an organophosphate, a pesticide, or insecticide and initiate appropriate containment and decontamination measures. In a similar manner, a sensor could be used at a given location to monitor pesticides and insecticides or to detect a biochemical or chemical warfare attack.

The assay of the present invention may be used to determine the amount of protection provided against exposure to a compound which affects the concentration or activity of AChE, BChE, or both such as a nerve agent in a subject by the administration of a protective inhibitor such as pyridostigmine bromide (e.g. FIG. 8A) or physostigmine.

The assay may be used to screen individuals for sensitivity to a drug. For example, an individual may be screened for succinylcholine sensitivity before general anesthesiology. This could be accomplished by ex vivo dosing of a patient's blood sample with the therapeutic level of succinylcholine used in surgery. The ratio of inhibition of this sample to that of the normal population would indicate whether the patient possesses the phenotypic BChE sensitivity.

Likewise, a subject may be screened for a disease such as cirrhosis of the liver or chronic drug abuse as these disease states selectively alter the concentration of AChE or BChE circulating in the blood. In particular, since AChE is biosynthesized in the liver, any disease state affecting liver function may exhibit a change in concentration of AChE. Also, chronic cocaine use has been demonstrated to decreases the plasma concentration of BChE. Therefore, one of ordinary skill in the art could monitor the treatment of chronic cocaine abusers by monitoring the blood levels of BChE as a function of time. Furthermore, any other disease state that selectively alters the levels or activities of AChE, BChE, or both, could likewise be screened for and monitored.

The change in red blood cell count of a subject may also be determined as the assay of the present invention may be used to detect a change in AChE concentration of about 2%, preferably about 1.5%. See e.g. FIG. 17. Since about 10% to about 12% of a subject's total blood volume is removed during blood donation and the levels of AChE and red blood cells are decreased after blood donation. The assay of the present invention can be used to screen individuals to determine if they are able to donate or if they donated blood recently. Likewise, the present invention may be used to determine if a subject suffers from anemia, thalassemias, spherocytosis, hemoglobin SS, hemolytic anemia, paroxysmal nocturnal hemoglobinuria, or megaloblastic anemia since these diseases either cause an increase or decrease in red blood cells count.

The assay may be used to determine whether a candidate compound affects the concentration or activity of AChE, BChE, or both. Any one interested in screening for a therapeutic agent could implement the assay of the invention in a much more relevant media such as blood. This would allow the determination of the effect that the candidate compound has, if any, on AChE, BChE, or both. Primary neuron cultures may also be used to screen for a therapeutic agent that may be neuroprotective. Candidate compounds to be screened may include those capable of providing nerve agent prophylaxis and those that transiently inhibit AChE, BChE, or both. For candidate compound screening, a stopped timed assay is preferred since the effect that the candidate demonstrates as a function of time is crucial and may be missed if a single arbitrary endpoint type assay is performed.

In addition to the stopped time assay, the effect of dilution on an inhibited sample must also be measured, since reversible non-covalently modifying compounds may be missed. This would occur in vitro since in the stopped time assay these compounds would display no catalytic turn-over and hence no activity return. In vivo due to elimination or clearance by the body, these reversible compounds would dissociate from AChE, BChE, or both and the activity of these proteins would increase. Body clearance can be mocked by dilution.

The assay of the invention may be adapted for use in a biosensor capable of detecting a agent such as a nerve agent, a chemical warfare agent, an organophosphate, an organophosphite, a pesticide, an insecticide, a carbamate, and the like. For example, a biosensor may contain known mixtures of AChE and BChE immobilized on a support which may then be placed in a given location or environment. Simultaneous monitoring and comparison of the rates of given substrates for AChE and BChE to that of a sealed chamber containing the same mixture of AChE and BChE, would provide real time information on the appearance or presence of the agent. The agent may be identified by comparing the rates of inhibition of AChE and BChE to those of a predefined database of rates for a variety of agents which affect the concentration or activity of AChE, BChE, or both. This biosensor may be used remotely from a given location to provide a buffer zone of early warning and detection. Alternately, first responders to a suspected chemical attack could use this biosensor to confirm and initiate appropriate containment and decontamination measures.

One may desire to remove any contaminants or compounds that may interfere with determining the activities and concentrations of AChE, BChE, or both in the test sample. Removal of a compound or a contaminant is desired when the presence of said compound changes activities and concentrations of AChE, BChE, or both in the test sample. A compound may potentially interfere with the assay of the present invention in that the compound may selectively alter the activity of AChE, BChE, or both (see e.g., FIGS. 1 and 3), or the compound may alter the molar extinction coefficient of the chromogenic substrate.

Figure 2:
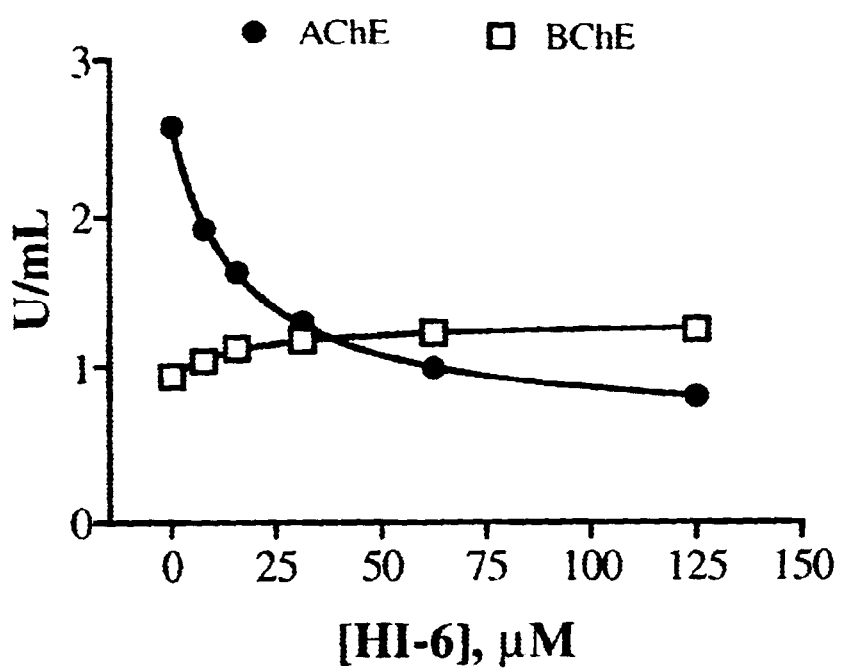
FIG. 2 is a graph which illustrates that AChE is inhibited while BChE is stimulated by small concentrations of HI-6, an oxime and part of the treatment regimes of Non-United States militaries for organophosphate and pesticide poisoning.

For example, if a blood test sample is analyzed to determine whether or not the subject from which the test sample was obtained was exposed to a nerve agent, a moderate decrease in the concentration of AChE, BChE, or both would be expected. However, as illustrated in FIG. 1, if the subject is administered an oxime, such as 2-PAM, the concentration of AChE is inhibited but BChE is unaffected. These alterations may cause the concentrations of AChE to appear to fall below the normal concentration range for individuals not exposed to a nerve agent. Even though the subject was not exposed to a low concentration or a small amount of a nerve agent a false positive would result. Alternatively, as shown in FIG. 2, treatment with an oxime, such as HI-6, which selectively inhibits AChE and stimulates BChE may cause the concentration of AChE, BChE, or both appear to be within a concentration range typical of individuals exposed to low levels or concentrations of a nerve agent, even though the subject was actually exposed to a much higher concentration. Thus, it would be desirable to remove the oxime from the test sample before analysis.

The removal of a compound or a contaminant may be done where one desires to monitor the concentration of AChE, BChE, or both in subject being treated with a compound, such as an oxime. For example, before one monitors the concentration of AChE, BChE, or both in a subject being treated with an oxime, one should remove the oxime from the test sample before analysis.

The removal of a compound or a contaminant may also remove the agonists or antagonists of AChE, BChE, or both. The removal of an agonist or antagonist does not affect the assay of the present invention where the agonist or antagonist (1) is irreversibly bound to AChE, BChE, or both and the binding results in an increase or a decrease in the cholinesterase activity, or (2) exhibits a slow disassociation or turnover rate with respect to the time scale of the assay and sample preparation. The removal of an agonist or antagonist will affect the assay of the present invention where the agonist or the antagonist exhibits a fast disassociation or turn-over rate. If the removal of an agonist or antagonist will affect the assay, one may analyze the test sample before removing the potentially interfering compound or contaminant and then analyze the test sample after removing the compound or contaminant. In any event, none of the currently accepted clinical methods remove said compounds prior to analysis.

The potentially interfering compound or contaminant may be removed by any suitable methods known in the art. For example, a spin column may be used to rapidly remove any free ligand from the complexed form by size exclusion. See e.g., FIG. 6B2.

Relative to the prior art assays, the assay of the present invention is rapid, accurate, and precise. Since the assay of the present invention is fast relative to prior art assays, the present invention may be adapted for use with high-throughput screening platforms such as the Biomeck 2000® (Beckman Coulter, Inc, Fullerton, Calif.) or any other such system known in the art. The present assay does not rely on the addition of selective AChE or BChE inhibitors, employs minimally invasive sampling techniques such as pricking the subject's finger, and provides results in less than about six minutes.

The present invention also relates to devices for detecting, measuring, or monitoring the activities and concentrations of AChE, BChE, or both, as the present assay may be adapted for use with diagnostic devices and computer software. Examples of suitable devices include hand held devices such as the commercially available i-STAT® system available from I-STAT Corporation, (Princeton, N.J.) or the Test-Mate OP™ unit available from EQM Research (Cincinnati, Ohio) as well as any other such device.

The present assay may be readily adapted to work with a device whose detection platforms are amperometric, UV/Visable, fluorescent or other. For example, an amperometric-based device, such as the i-STAT® system, may be adapted by replacing the chromogenic substrate with a substrate that produces a given equivalent of hydrogen peroxide per catalytic cycle which can be monitored amperometrically using standard methods known in the art. Further a micro-fluidic cartridge such as those available for use with the i-STAT® system may be developed or modified to comprise all the reagents, such as buffer, standards and substrates, for performing the assay of the present invention. A sterile lancet for blood sampling may also be included with or in the device. The device may be programmed or designed to automatically perform all the necessary test sample dilutions when the cartridge is inserted.

The present assay may be used for high throughput screening and adapted for use with benchtop equipment such as the Biomeck 2000 or other such systems known in the art. For example, A Biomeck 2000 possessing circulating reagent reservoirs, single and multi-channel pipettes, a gripper tool for labware movement and placement, a plate and tip stacker carousel, and an integrated mictrotiter plate reader would allow all necessary sample dilutions, equipment placement, reagent addition, and velocity measurements comprised in the present invention to be carried out automatically.

The assay of the invention may also be used for normalizing sample data for direct comparison to that of a given population by measuring an internal standard property of the sample and referencing that value to that of the given population, this normalization constant is then used to directly modify the measured concentrations of activity of acetylcholinesterase, butyrylcholinesterase, or both.

In the following examples, acetylthicholine iodide (ATC), propionylthiocholine iodide (PTC), butyrylthiocholine iodide (BTC), 4,4'-dithiopyridine (DTP), and tetraisopropylphosphoramide (Iso-OMPA) were purchased from Sigma Chemical Co. Racemic huperzine-A (rac Hup-A) was purchased from CalBiochemical-NovaBiochem Corporation (San Diego, Calif.). Water was polished to 18.2 MΩ by passage through a Millipore water purification system (Millipore, Bedford, Mass.). Intra-venous blood was obtained from ten human volunteers and stored in heparin vacutainers® (BD Vacutainer Systems, Annapolis, Md.). Intra-venous blood was obtained from ten Rhesus monkeys (Walter Reed Army Insititute of Research, Division of Veterinary Medicine, Silver Spring, Md.) and stored in heparin vacutainers®. Whole blood samples from 10 Sprague Dawley rats (Charles River Laboratories, Wilmington, Mass.) were obtained and stored in heparin vacutainers®. Trunk blood obtained from 10 Hartley guinea pigs (Charles River Laboratories, Wilmington, Mass.) was stored in the presence of EDTA. All blood samples were refrigerated at 4° C. until used.

While the detailed description and following examples are directed to an assay for acetylcholinesterase, butyrylcholinesterase, or both, the present invention is not limited to acetylcholinesterase and butyrylcholinesterase, but includes any assay for any protein which belongs to a plurality of proteins which have similar or overlapping properties towards a plurality of substrate.

EXAMPLE 1

Sample Preparation for Cholinesterase Assay

A. Blood Sample

A sample of blood is obtained from a subject and appropriately treated with a suitable anticoagulant known in the art. If the blood sample is to be stored and screened later and the sample is time sensitive, it may be flash frozen in a liquid nitrogen bath and stored at −80° C. A sample that is not time sensitive may be stored at 4° C.

When ready for screening, 20 μL of the blood sample is transferred to a 200 μL PCR tube containing 140 μL of 18.2 MΩ water with a positive displacement pipette. Then the sample is mixed thoroughly by any suitable method such as pipetting or vortexing. When mixed thoroughly, the sample may be analyzed as set forth in Example 2. It is important to note that the actual dilutions to be used are specific for a given population, species or sample group. The dilutions used here were for 20 μL of Hartley guinea pig blood diluted with 140 μL of water or 10 μL of human blood diluted with 190 μL of water.

B. Tissue Sample

It is preferred that the tissue sample is obtained from a $CO_2$ anesthetized subject since some anesthetics inhibit AChE, BChE, or both. The tissue sample is flash frozen on powdered dry ice. The tissue sample or a fraction thereof is weighed and minced. The minced sample is quantitatively transferred to a plastic tube and 4 volumes (w/v) of 50 mM sodium phosphate buffer at pH 8.00 is added. The sample is homogenized 5 times for about 3 seconds each with an electric homogenizer at full RPM. The crude homogenate is transferred to a glass ground hand homogenizer and thoroughly pulverized as per the manufacture's directions. A 160 μL aliquot of the sample is transferred to a 200 μL PCR tube and may be analyzed as set forth in Example 2. The remaining homogenate may be stored for later use. Again, it is important to note that the actual dilutions to be used are specific for a given population, species or sample group. The dilutions used here were for Hartley guinea pig diaphragm.

EXAMPLE 2

Cholinesterase Assay

The following stock reagents ATC, PTC, BTC, DTP and buffer were prepared and stored at −20° C. until needed, or stored at 4° C. when in use: ATC=30 mM acetylthiocholine prepared in 18.2 MΩ water, PTC=30 mM propionylthiocholine prepared in 18.2 MΩ water, BTC=30 mM butyrylthiocholine prepared in 18.2 MΩ water, DTP=6 mM 4,4'-dithiopyridine prepared in 10% HPLC grade methanol/50 mM sodium phosphate buffer, pH 8.00, buffer=50 mM sodium phosphate buffer, pH 8.00.

The following working reagents A, B, D and P were prepared and stored at 25° C. or room temperature: A=1.0 mM acetylthiocholine and 200 μM 4,4'-dithiopyridine (8.40 μL of buffer, 300 μL of ATC, 300 μL of DTP), P=1.0 mM propionylthiocholine and 200 μM 4,4'-dithiopyridine (8.40 mL of buffer, 300 μL of ATC, 300 μL of DTP), B=1.0 mM butyrylthiocholine and 200 μM 4,4'-dithiopyridine (8.40 mL of buffer, 300 μL of ATC, 300 μL of DTP), D=200 μM 4,4'-dithiopyridine (8.40 mL of buffer, 300 μL of 18.2 MΩ water, 300 μL of DTP).

A microtiter plate spectophotometer such as Molecular Devices Spectramax Plus® microtiter plate spectrophotometer available from Molecular Devices Corporation (Sunnyvale, Calif.) was used. Two experiments were performed on the same plate. For the first experiment, it was indicated that it was a kinetic assay and the parameters set were: 1) 324 nm wavelength, 2) 60 second pre-read shaking, 3) 3 second shaking between reads, 4) 4 minute collection time, and 5) linear least squares data analysis. For the second experiment, it was indicated that it was an endpoint assay and the parameters set were 1) two wavelengths, 415 nm and 445 nm and 2) 5 second pre-read shaking.

Test samples obtained from either Hartley guinea pigs or humans were mixed five times by pipetting. 10 μL of each test sample was dispensed into each column of a 96 well microtiter plate (i.e., 8 test samples were dispensed into 12 columns=96 wells). 290 μL aliquots of working reagent D (control) were added to columns 1–3, 290 μL aliquots of working reagent A (acetylthiocholine) were added to columns 4–6, 290 μL aliquots of working reagent P (propionylthiocholine) were added to columns 7–9, and 290 μL aliquots of working reagent B (butyrylthiocholine) were added to columns 10–12 with a multichannel electronic pipette.

The absorbencies and the kinetic rates of the test samples were obtained. To account for well-to-well variation due to pipetting error within a sample (i.e., the twelve wells that constitute one row of a standard 96 well microtiter plate), each well rate was multiplied by a correction factor. This correction factor was the ratio of the average absorbency of the test sample, i.e., the average of the twelve wells ($A_{415}$ for human or $A_{445}$ for guinea pig) to the observed absorbance for the well being treated. The ensuing values were used to calculate the concentrations of AChE and BChE by solving the following three sets of equations:

Equation Set 1

$$ATC \text{ rate} = x_1[AChE] + y_1[BChE]$$
$$BTC \text{ rate} = x_3[AChE] + y_3[BChE]$$

Equation Set 2

$$ATC \text{ rate} = x_1[AChE] + y_1[BChE]$$
$$PTC \text{ rate} = x_2[AChE] + y_2[BChE]$$

Equation Set 3

$$PTC \text{ rate} = x_2[AChE] + y_2[BChE]$$
$$BTC \text{ rate} = x_3[AChE] + y_3[BChE]$$

These equations may be solved by any method known in the art such as linear combination. The sensitivity coefficients, $x_1$–$x_3$ and $y_1$–$y_3$, were determined as described in Example 3. In the above equations, the sensitivity coefficients for AChE are $x_1$, $X_2$, and $X_3$ and correspond to ATC, PTC, and BTC, respectively. Similarly, $y_1$, $y_2$, and $y_3$ denote the BChE sensitivity coefficients. All rates were corrected for spontaneous hydrolysis of DTP by blood and are expressed in terms of change in absorbance with respect to time (e.g., mAbs/min). The units of the sensitivity coefficients are mAbs/min/sample dilution, and the concentrations of AChE and BChE obtained via equation sets 1 through 3 are unitless pure numbers.

Final numerical processing began with evaluating the mean and standard deviation for AChE and BChE from the three independently determined concentrations of AChE and BChE. These values were transformed from pure numbers into mAbs/min/sample dilution by multiplying the mean and standard deviation by the appropriate sensitivity coefficient. For example, to convert the calculated concentration of AChE into mAbs/min/sample dilution, the mean and standard deviation were multiplied by $x_1$, the ATC AChE sensitivity coefficient for AChE. In a similar manner, the calculated concentration of BChE was transformed into mAbs/min/sample dilution, by multiplying each value by y3, the BTC sensitivity coefficient for BChE. It is important to realize that any of the protein's sensitivity coefficients could be used for this process (i.e., $x_1$–$x_3$ for AChE/$y_1$–$y_3$ for BChE), however, the final results will represent the turnover of that sensitivity coefficient's corresponding substrate (e.g., $X_2$ turnover of PTC by AChE).

The data was then corrected to a 1-cm pathlength by taking into account the pathlength to volume ratio of a well in the microtiter plate being used (i.e., the 300 μL total well volume corresponded to 0.89 cm). In addition all test sample dilutions were accounted which included the dilutions of the sample due to sample processing, see Example 1, and reagent addition, see above. In the case of guinea pig blood, 20 μL of blood was mixed with 140 μL of water producing an 8-fold dilution. In addition to this dilution, 290 μL of working reagent was mixed with 10 μL of sample for a 30-fold dilution. Therefore, the sample was diluted a total of 240 fold. In the case of human blood, 10 μL of blood was mixed with 190 μL of water producing a 20-fold dilution. In addition to this dilution, 290 μL of working reagent was mixed with 10 μL of sample for a 30-fold dilution. Therefore, the sample was diluted a total of 600 fold. Thus, the concentrations of AChE and BChE determined above were divided by the pathlength and multiplied by the total dilution. Finally, the data was converted from mAbs/min to U/mL, wherein 1 U/mL corresponds to the turnover of 1 μmol of substrate/min at 1 mM substrate concentration using standard methods known in the art.

Moreover, the results can be normalized to the average population by multiplying the AChE and BChE concentrations by the ratio of the calculated or predetermined average population $A_{415}$ ($A_{445}$) to that of the sample's $A_{415}$ ($A_{445}$) (i.e., the average absorbency for all twelve wells in one row corresponding to the sample in question). This method accounts for volumetric errors introduced by the technician, since both AChE and BChE are being modified by the same ratio. Alternatively, one could selectively multiply the AChE results by the aforementioned ratio to account for hematocrit variations. Likewise, since plasma has absorption around 240 nm, a similar correction could be applied selectively to the BChE values.

Table 1A shows that the precision of the assay for Hartley guinea pig is constant at 0.003 U/mL for both AChE and BChE corresponding to a precision of less than about 0.8% and about 0.3% for uninhibited AChE and BChE, respectively. Due to the constant nature of the error, increasing the extent of inhibition increases the uncertainty associated with knowing the true value, however, a working range of inhibition from about 0% to about 99% is still clearly demonstrated for both AChE and BChE.

TABLE 1A

|  | AChE (U/mL) | | BChE (U/mL) | |
| --- | --- | --- | --- | --- |
|  | Average | STD | Average | STD |
| [rac Hup-A] nM | | | | |
| 56 | 0.006 | 0.004 | 0.907 | 0.004 |
| 28 | 0.019 | 0.002 | 0.929 | 0.002 |
| 14 | 0.055 | 0.003 | 0.912 | 0.001 |
| 7.03 | 0.136 | 0.002 | 0.892 | 0.002 |
| 3.52 | 0.214 | 0.002 | 0.907 | 0.002 |
| 1.76 | 0.334 | 0.002 | 0.930 | 0.003 |
| 0.88 | 0.462 | 0.001 | 0.913 | 0.002 |
| 0.00 | 0.610 | 0.007 | 0.925 | 0.004 |

TABLE 1A-continued

|  | AChE (U/mL) | | BChE (U/mL) | |
| --- | --- | --- | --- | --- |
|  | Average | STD | Average | STD |
| [Iso-OMPA] nM | | | | |
| 320 | 0.605 | 0.007 | 0.048 | 0.003 |
| 160 | 0.630 | 0.003 | 0.071 | 0.001 |
| 80 | 0.616 | 0.001 | 0.080 | 0.001 |
| 40 | 0.635 | 0.004 | 0.143 | 0.001 |
| 20 | 0.657 | 0.004 | 0.279 | 0.005 |
| 10 | 0.585 | 0.004 | 0.565 | 0.003 |
| 5 | 0.597 | 0.005 | 0.699 | 0.001 |
| 0 | 0.582 | 0.008 | 0.945 | 0.004 |

FIG. 3A1 is a graph that shows the concentration of AChE and BChE in Hartely guinea pig blood as a function of titration with rac Hup-A. FIG. 3B1 is a the concentration of AChE and BChE in Hartley guinea pig blood as graph that shows the concentration with Iso-OPMA. Note that FIG. 3A1 illustrates the selective nature of rac Hup-A, and FIG. 3B1 likewise illustrates the selective nature of Iso-OMPA.

Table 1B and FIG. 3A2 panels A–D show representative data for human whole blood titrated rac Hup-A, Iso-OMPA, and combination mixtures of rac Hup-A and Iso-OMPA. The table demonstrates several other key details of the assay. First, the precision of the assay for human blood is constant at about 0.01 U/mL regardless of inhibitor for both AChE and BChE. This corresponds to a precision of less than about 0.83% about 0.34% for uninhibited AChE and BChE, respectively. Second, due to the constant nature of the error, increasing the extent of inhibition increases the uncertainty associated with knowing the true value, however, a working range of inhibition from about 0% to about 99% is still clearly demonstrated for both AChE and BChE. Third, the inter run variability was about 1.9% and about 1.0% for AChE and BChE, respectively. The AChE value was obtained by evaluating the % CV for all BChE samples in the presence and absence of Iso-OMPA (i.e., Iso-OMPA does not affect AChE concentration). Likewise, the BChE value refers to the % CV for all BChE values obtained in the presence and absence rac Hup-A. Finally, mixture of selective AChE and BChE inhibitors produce identical results to those obtained with the isolated pure inhibitor. See FIG. 3A2.

TABLE 1B

|  |  |  | Inhibitor/Inhibitor Mixture | | | | | |
| --- | --- | --- | --- | --- | --- | --- | --- | --- |
|  |  |  | Hup-A | | Iso-OMOA & Hup-A | | Iso-OMPA | |
|  | [Hup-A], nM | [Iso-OMPA],nM | Average | Stdev | Average | Stdev | Average | Stdev |
| AChE, U/mL | 56 | 1280 | 0.292 | 0.027 | 0.315 | 0.003 | 4.181 | 0.015 |
|  | 28 | 640 | 0.354 | 0.005 | 0.397 | 0.010 | 4.085 | 0.020 |
|  | 14 | 320 | 0.640 | 0.007 | 0.642 | 0.008 | 4.079 | 0.023 |
|  | 7 | 160 | 1.158 | 0.010 | 1.108 | 0.014 | 3.974 | 0.020 |
|  | 4 | 80 | 1.809 | 0.001 | 1.761 | 0.010 | 3.992 | 0.024 |
|  | 2 | 40 | 2.459 | 0.005 | 2.378 | 0.021 | 4.010 | 0.017 |
|  | 1 | 20 | 3.172 | 0.016 | 3.067 | 0.015 | 3.980 | 0.015 |
|  | 0 | 0 | 3.947 | 0.025 | 4.029 | 0.020 | 3.973 | 0.006 |
| BChE, U/mL | 56 | 1280 | 2.676 | 0.011 | 0.847 | 0.003 | 0.875 | 0.007 |
|  | 28 | 640 | 2.609 | 0.005 | 1.567 | 0.005 | 1.491 | 0.008 |
|  | 14 | 320 | 2.638 | 0.006 | 2.068 | 0.004 | 2.054 | 0.010 |
|  | 7 | 160 | 2.633 | 0.009 | 2.347 | 0.012 | 2.318 | 0.018 |
|  | 4 | 80 | 2.617 | 0.016 | 2.495 | 0.009 | 2.440 | 0.009 |
|  | 2 | 40 | 2.612 | 0.013 | 2.563 | 0.009 | 2.509 | 0.009 |
|  | 1 | 20 | 2.600 | 0.005 | 2.586 | 0.007 | 2.572 | 0.005 |
|  | 0 | 0 | 2.653 | 0.007 | 2.633 | 0.002 | 2.636 | 0.006 |

In Table 1B, inhibitor concentrations correspond to those in undiluted whole blood. The samples were incubated at room temperature for three hours.

FIG. 3A2 is a graph that shows the concentration of AChE and BChE in human blood as a function of titration with rac Hup-A. FIG. 3B2 is a graph that shows the concentration of AChE and BChE in human blood as a function of titration with Iso-OPMA. FIG. 3C2 is a graph that depicts the concentration of AChE as a function of rac Hup-A contained in the combined inhibitor mixtures. FIG. 3D2 illustrates the response of BChE as a function of Iso-OMPA concentration present in the combined mixtures. Note that FIGS. 3A1, 3A2 and 3C2 illustrate the selective nature of rac Hup-A, while FIGS. 3B1, 3B2 and 3D2 similarly illustrate the selective nature of Iso-OMPA

EXAMPLE 3

Sensitivity Coefficient Determination: Method 1

The sensitivity of AChE and BChE towards ACT, PTC, and BTC was established as detailed below for Hartley guinea pig.

A stock solution of 900 nM rac Hup-A was prepared in 18.2 MΩ water. A stock solution of 5.12 μM Iso-OMPA was prepared in 18.2 MΩ water. A stock solution of 900 nM Hup-A and 5.12 μM Iso-OMPA (Hup-A/Iso-OMPA) was prepared in 18.2 MΩ water.

Serial dilutions of the Hup-A stock solution were prepared and resulted in concentrations of 900, 450, 225, 113, 56, 28, 14, and 0 nM of Hup-A. Serial dilutions of the Iso-OMPA stock solution were prepared and resulted in concentrations of 5120, 2560, 1280, 640, 320, 160, 80, and 0 nM of Iso-OMPA. Serial dilutions of the Hup-A/Iso-OMPA stock solution were prepared and resulted in concentrations of 900, 450, 225, 113, 56, 28, 14, and 0 nM of Hup-A and 5120, 2560, 1280, 640, 320, 160, 80, and 0 nM of Iso-OMPA, respectively.

For each species, ten different whole blood samples were obtained and then pooled together. Each whole blood sensitivity coefficient sample was the pooled whole blood sample and represented an average sample for each given species. Serial dilutions of each sensitivity coefficient sample were prepared in 18.2 MΩ water and resulted in concentrations of 0.5, 0.25, 0.125, 0.063, 0.031, 0.016, 0.008, and 0.004 (volume: volume).

Generally, each sensitivity coefficient sample, the serial dilutions described above, was titrated with the inhibitor, rac Hup-A. Then the activity of an aliquot of each sensitivity coefficient sample after a three-hour incubation at room temperature was measured in the presence of acetylthiocholine. This was repeated for propionylthiocholine (PTC), butyrylthiocholine (BTC), and finally 4,4'-dithiopyridine (DTP). At infinite inhibitor concentration, the activity of the AChE component was selectively eliminated, and the residual activity was solely from BChE. Analysis of the measured substrate rates (ATC, PTC, BTC) in the absence and presence of infinite inhibitor, corrected for background hydrolysis (DTP), as a function of serial dilution produced linear relationships corresponding to control (Vc) and residual (Vr) rates, respectively. See FIGS. 10A–B for ATC/rac Hup-A results. The slope of each Vr line represented the sensitivity of BChE for each substrate. The sensitivity of AChE for each substrate was obtained by subtracting the sensitivity of BChE from the corresponding slopes of the control reactions, Vc.

The previously described titration was repeated using Iso-OMPA. This time the slope of the line for the residual activities (i.e., in the presence of infinite inhibitor, Vr) represented the sensitivity of AChE for each substrate. The sensitivity of BChE for each substrate was obtained by subtracting the sensitivity of AChE from the corresponding slopes of the control reactions, Vc.

Specifically, the stock and working reagents as set forth in Example 2 were used. A microtiter plate spectophotometer such as Spectramax Plus microtiter plate spectrophotometer was used. Two assays were performed on each sample. The first was a kinetic assay possessing the following parameters: 1) 324 nm wavelength, 2) 60 second pre-read shaking, 3) 3 second shaking between reads, 4) a 4 minute collection time, and 5) linear least squares data analysis. Upon completion of the first assay, the second, an endpoint assay, was done using the following parameters: 1) two wavelengths, 415 nm and 445 nm and 2) a 5 second pre-read shaking.

The activity of the control vs. the concentration of each blood sensitivity coefficient sample was determined. The $A_{415}$ and $A_{445}$ vs. blood concentration were determined and the most appropriate range of blood concentrations was used. It is desirable to have the high end linear over 4 minutes and have enough signal over the low end such that the titration with Hup-A/Iso-OMPA can clearly be resolved from the baseline. See FIGS. 10A–B ATC/rac Hup-A results. It is also desirable to consider a blood range in which the relationship of $A_{415}$ or $A_{445}$ vs. the blood concentration is linear in order to normalize the data. See FIG. 11.

After the appropriate concentration range was determined, 4 or 5 serial dilutions of the pooled whole blood spanning the appropriate concentration were prepared. The volume of each dilution was 4 mL.

150 μL aliquots of each blood dilution were mixed with 10 μL aliquots of each dilution of Hup-A, Iso-OMPA, and Hup-A/Iso-OMPA and incubated at room temperature for 3 hours on a plate rocker. After incubation, the sensitivity coefficient samples were mixed five times in the PCR tubes by pipetting. 10 μL of each sensitivity coefficient sample were dispensed into each column of a 96 well microtiter plate (i.e., 8 sensitivity coefficient samples were dispensed into 12 columns=96 wells, corresponding to one blood dilution at eight inhibitor concentration). 290 μL aliquots of working reagent D (background) were added to columns 1–3, 290 μL aliquots of working reagent A (acetylthiocholine) were added to columns 4–6, 290 μL aliquots of working reagent P (propionylthiocholine) were added to columns 7–9, and 290 μL aliquots of working reagent B (butyrylthiocholine) were added to columns 10–12 with a multichannel electronic pipette. The rates of hydrolysis and the absorbancies of the sensitivity coefficient samples were measured as described above. Each substrate rate was corrected for spontaneous background hydrolysis of DTP. The activity of the control vs. the concentration of each blood sensitivity coefficient sample was determined and plotted on a graph. This was repeated for each remaining blood dilution and inhibitor/inhibitor mixtures. See FIG. 10A for ATC/rac Hup-A results.

Each titration for each substrate and each inhibitor (Hup-A, Iso-OMPA, Hup-A/Iso-OMPA) was fitted to the following equation:

$$V_{obs} = \frac{(Vc - Vr)K_I}{K_I + [I]} + Vr$$

in which Vc and Vr refer to the velocities at 0 and infinite inhibitor concentration, respectively, and $K_I$ refers to the observed inhibition constant. Vc, Vr, and $K_I$ are obtained by fitting the observed velocities vs. inhibitor concentration using non-linear least squares fitting procedures known in the art. The control activities, Vc, and the residual activities, Vr, were tabulated and used in subsequent calculations.

For each substrate the control activities, Vc, vs. blood dilution, and the residual activity, Vr, vs. blood dilution were plotted on a graph for each type of inhibitor. See FIG. 10B for ATC/rac Hup-A results. At an absorbance of 415 nm vs. the blood concentration, the average slope and intercept for: human were 31.785 and 0.027; Rhesus monkey were 30.460 and 0.038. At an absorbance of 445 nm vs. the blood concentration, the average slope and intercept for: Hartley guinea pig were 4.500 and 0.027 (FIG. 11); Sprague Dawley rat were 5.269 and 0.017. These values permit normalizing any given sample to that of the average population as previously described in Example 2. All measured velocities possessed units of mAbs/min, while all measured absorbances are in standard absorbance units.

The sensitivity coefficient samples (i.e., the pooled whole blood serial dilutions previously described) titrated with the inhibitor solutions comprising both Hup-A and Iso-OMPA previously detailed established that about 100% of the ChE activity was due to AChE and BChE.

The sensitivity coefficients of AChE and BChE for ATC, PTC, and BTC for Hartley guinea pig as determined for each specific cholinesterase inhibitor are set forth in Table 2. The average of said sensitivity coefficients are also tabulated. It is important to note that these values may not be identical to those determined by another lab since the pooled blood sample will not have an identical cholinesterase composition due to individual sample population variation of AChE and BChE. However, this is not critical to the assay of the present invention since these values only reflect the content of AChE and BChE of the pooled sample. The actual concentrations of each protein as determined by Example 2, however, remain the same or substantially similar regardless of the sensitivity coefficients used, provided that the sensitivity coefficients were obtained from the same species being tested.

TABLE 2

| Species | Substrate | AChE Coefficient (mAbs/min/[blood]) | | BChE Coefficient (mAbs/min/[blood]) | |
|---|---|---|---|---|---|
| | | Value | Error | Value | Error |
| Hartley Guinea Pig: rac Hup-A Titration | | | | | |
| | ATC | 444 | 8 | 270 | 4 |
| | PTC | 226 | 16 | 518 | 12 |
| | BTC | 43 | 13 | 515 | 9 |
| Hartley Guinea Pig: Iso-OMPA Titration | | | | | |
| | ATC | 418 | 14 | 297 | 16 |
| | PTC | 194 | 36 | 550 | 37 |
| | BTC | 0 | 1 | 557 | 10 |
| Hartley Guinea Pig: Average of rac Hup-A & Iso-OMPA Titrations | | | | | |
| | ATC | 431 | 19 | 284 | 19 |
| | PTC | 210 | 23 | 534 | 23 |
| | BTC | 21 | 30 | 536 | 30 |

EXAMPLE 4

Sensitivity Coefficient Determination: Method 2

The sensitivity of AChE and BChE towards ATC, PTC, and BTC was established using a modification of the procedure outline in Example 3 for Hartley guinea pig, human, Rhesus monkey, and Sprague Dawley rat. The advantage of this method is faster processing time and one-third less sensitivity coefficient sample needs to be obtained.

Specifically the procedure is analogous to that in Example 3 except that only the Hup-A titration is performed. All remaining steps including sample preparation, data collection, and data analysis remain the same. The sensitivity coefficients of AChE and BChE for ATC, PTC, and BTC for Hartley guinea pig, human, Rhesus monkey, and Sprague Dawley rat blood determined using this method are set forth in Table 3.

TABLE 3

| Species | Substrate | AChE Coefficient (mAbs/min/[blood]) | | BChE Coefficient (mAbs/min/[blood]) | |
|---|---|---|---|---|---|
| | | Value | Error | Value | Error |
| Human | | | | | |
| | ATC | 2162 | 68 | 841 | 17 |
| | PTC | 1071 | 32 | 1417 | 16 |
| | BTC | 82 | 3 | 1466 | 37 |

TABLE 3-continued

| Species | Substrate | AChE Coefficient (mAbs/min/[blood]) | | BChE Coefficient (mAbs/min/[blood]) | |
|---|---|---|---|---|---|
| | | Value | Error | Value | Error |
| Rhesus monkey | | | | | |
| | ATC | 1599 | 99 | 314 | 17 |
| | PTC | 844 | 25 | 514 | 85 |
| | BTC | 0 | 0 | 661 | 45 |
| Hartley Guinea Pig | | | | | |
| | ATC | 294 | 12 | 321 | 3 |
| | PTC | 151 | 22 | 554 | 15 |
| | BTC | 0 | 4 | 558 | 3 |
| Sprague Dawley Rat | | | | | |
| | ATC | 282 | 21 | 103 | 8 |
| | PTC | 158 | 15 | 134 | 8 |
| | BTC | 0 | 0 | 62 | 2 |

EXAMPLE 5

Stopped Time Assay

The assay of the present invention may be used to determine the kinetics of inhibition for a non-selective inhibitor, such as a non-selective cholinesterase inhibitor, or a selective inhibitor. It is noted that extremely short time intervals of about 30 seconds or the limiting speed of the human technician may be monitored by the assay of the present invention.

Rhesus monkey blood was used in a modified stopped-time assay wherein the activities and concentrations of AChE and BChE were determined with 8 different concentrations of pyridostigmine bromide (PB) were determined as a function of time. Serial PB dilutions were prepared in whole blood and resulted in concentrations of 10.0, 5.0, 2.5, 1.25, 0.63, 0.31, 0.16, and 0 $\mu$M of pyridostigmine bromide.

Figure 4:
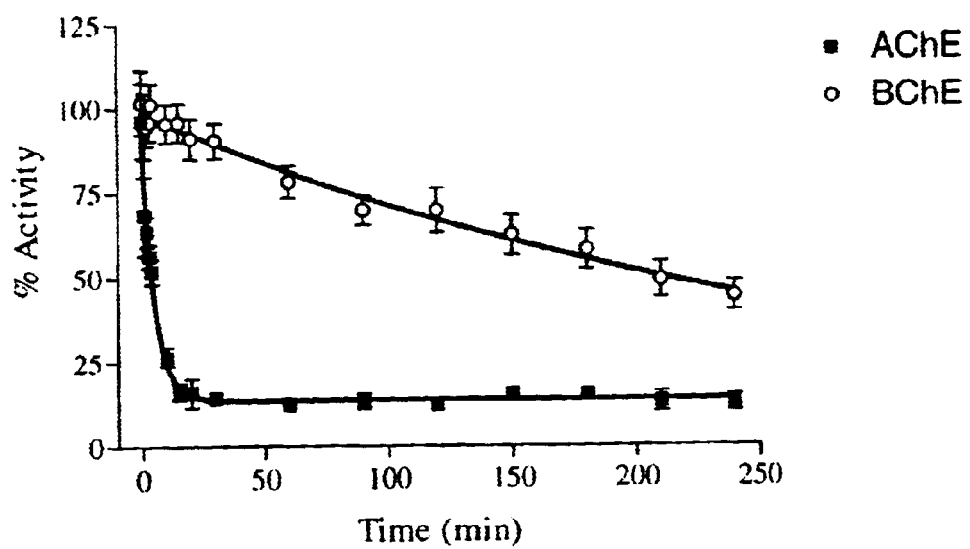
FIG. 4 is a graph demonstrating the simultaneous ex vivo inhibition of Rhesus monkey whole blood AChE and BChE with 2.5 $\mu M$ pyridostigmine bromide, PB, as a function of time.

10 $\mu$L aliquots of the eight resulting mixtures were transferred into 200 $\mu$L PCR tubes. The PCR tubes were flash frozen on dry ice at 0, 1, 2, 3, 4, 5, 10, 15, 20, 30, 60, 90, and at periods of time up to about 12500 minutes to prevent further inhibition or activity return. Then each test sample was assayed for ATC, PTC and BTC activity according to Example 2. Then the concentrations of AChE and BChE were calculated for each time interval and test sample. FIG. 4 is a graph that shows the activities of AChE and BChE in Rhesus monkey blood affected by 2.5 $\mu$M of PB as a function of time.

EXAMPLE 6

Chemical Warfare Agent Titration

16 Biorad P6 spin columns (Bio-Rad Laboratories Hercules, Calif.) were prepared according to the manufacture's directions. Serial dilutions of soman (GD) were prepared in saline and resulted in concentrations of $1.00 \times 10^{-6}$, $8.00 \times 10^{-7}$, $6.40 \times 10^{-7}$, $5.12 \times 10^{-7}$, $4.10 \times 10^{-7}$, $3.28 \times 10^{-7}$, $2.62 \times 10^{-7}$, $2.10 \times 10^{-7}$, $1.68 \times 10^{-7}$, $1.34 \times 10^{-7}$, $1.07 \times 10^{-7}$, $8.59 \times 10^{-8}$, and 0 M of GD.

200 $\mu$L aliquots of the GD serial solutions were placed into fourteen 1.5 mL microfuge tubes. Then 100 $\mu$L aliquots of human whole blood were added to each of the 14 tubes. The resulting blood solutions were mixed by vortexing and then incubated at room temperature for 2 hours. The cholinesterase assay as described in Example 2 was performed.

Figure 5:
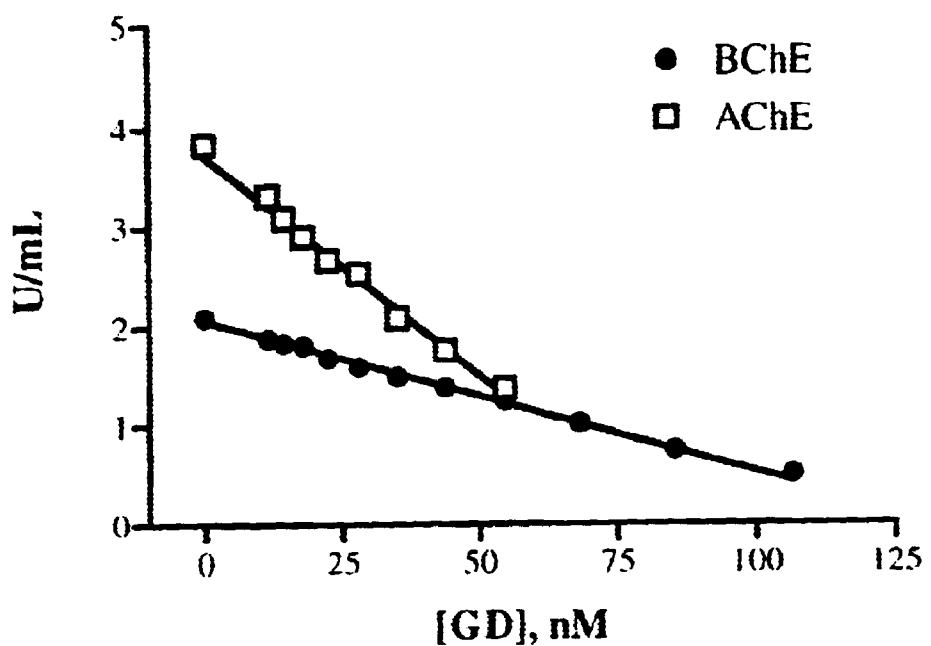
FIG. 5 is a graph demonstrating the simultaneous ex vivo titration of human blood AChE and BChE with the chemical threat agent soman, GD.

The concentrations of AChE and BChE were calculated for each test sample as described in Example 2. FIG. 5 is a graph that shows the concentrations of AChE and BChE in human blood as a function of titration with GD. FIG. 5 is intended to illustrate that the specific effects exerted on AChE and BChE by a relatively non-specific antagonist can be monitored using the procedure detailed in Example 2. Note that only the linear portion of each titration are depicted for clarity.

EXAMPLE 7

Oxime Titration

A. 2-PAM

A stock solution of 2-PAM prepared in 18.2 MΩ water was prepared. Serial dilutions of the stock solution were prepared having the following concentrations: 0.5, 0.25, 0.125, 0.063, 0.016, 0.008, and 0.000 M. Next, 10 $\mu$L aliquots of each dilution were added to the wells of a microtiter plate followed by the addition of 150 $\mu$L aliquots of 8× diluted Hartley guinea pig blood. After thorough mixing, the test samples were assayed as described in Example 2. The background hydrolysis of DTP, ATC, PTC, and BTC was measured without blood present. These values were subtracted from the blood values prior to calculating the concentrations of AChE and BChE as per Example 2. The results were calculated and graphed as illustrated in FIG. 1.

B. HI-6

A stock solution of HI-6 prepared in 18.2 MΩ water was prepared. Serial dilutions of the stock solution were prepared having the following concentrions: 0.450, 0.225, 0.112, 0.056, 0.028, 0.014, 0.007, and 0.000 $\mu$M. Next, 10 $\mu$L aliquots of each dilution were added to the wells of a microtiter plate followed by the addition of 150 $\mu$L aliquots of 20× diluted Rhesus monkey blood. After thorough mixing, the test samples were assayed as described in Example 2. The background hydrolysis of DTP, ATC, PTC, and BTC was measured without blood present. These values were subtracted from the blood values prior to calculating the concentrations of AChE and BChE as per Example 2. The results were calculated and graphed as illustrated in FIG. 2.

EXAMPLE 8

Removal of Impurities in Samples

To demonstrate the efficacy of removing small organic molecules from a blood matrix using spin columns based on size exclusion chromatography, three separate experiments were preformed. In the first experiment, Biorad P6 spin columns removed high concentrations of small organic molecules. In the second experiment, variously diluted thoroughly lysed whole blood samples were applied to individual Biorad P6 spin columns. The effluents from these columns as well as their parent blood dilutions were assayed for cholinesterase content as described in Example 2. In the third experiment, A Biorad P6 spin column was used to separate PB inhibited ChE in whole human blood from free excess PB. A stopped time assay was performed on the column effluent as well as an untreated matched control. The assay described in Example 2 was used to monitor the increase in AChE concentration as a function of time.

The results clearly demonstrate the feasibility of applying thoroughly lysed whole blood samples to spin columns with little cholinesterase retention and full uncomplexed ligand removal. The following examples demonstrate one potential method for removing interfering compounds from a sample. It is noted, however, that other methods known in the art may be used to remove interfering compounds from a sample.

A. Removal of GD by Biorad P6 Spin Columns

To determine whether spin columns can effectively remove an impurity such as GD from a test sample, Biorad P6 spin columns were used as per the manufacturer's directions.

Figure 6A:
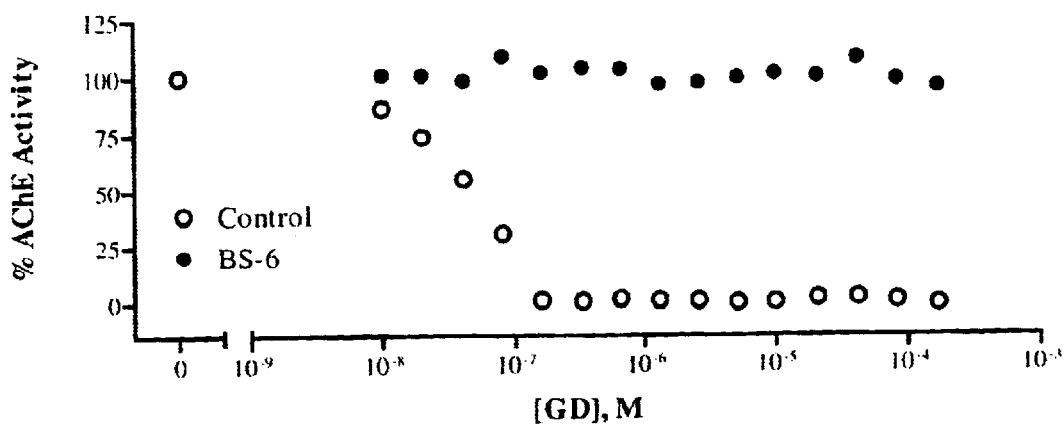
FIG. 6A shows a graph that illustrates that a small AChE antagonist such as soman (GD) can be effectively removed by using spin column purification.
Figure 6B:
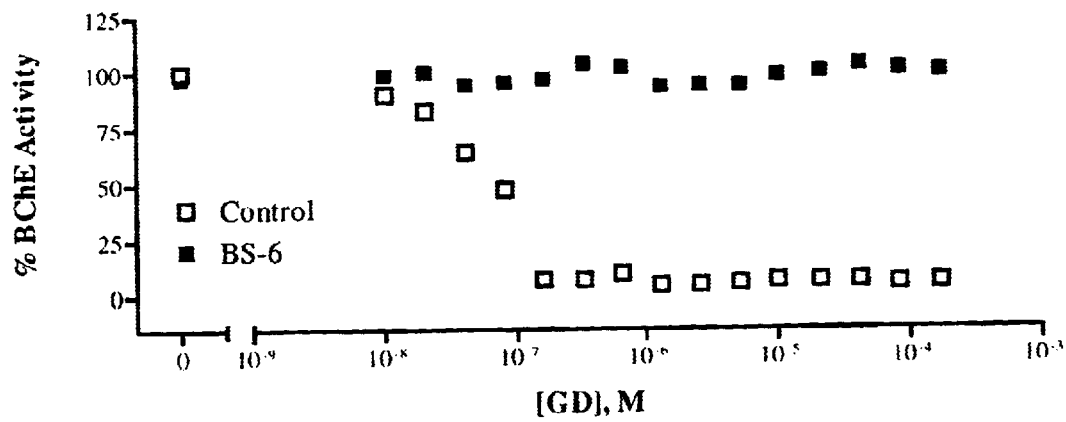
FIG. 6B shows a graph that illustrates that a small BChE antagonist such as GD can be effectively removed by using spin column purification.

Sixteen GD dilutions possessing the following concentrations were prepared in saline: $1.0 \times 10^{-3}$, $5.0 \times 10^{-4}$, $2.5 \times 10^{4}$, $1.3 \times 10^{-4}$, $6.3 \times 10^{-5}$, $3.1 \times 10^{-5}$, $1.6 \times 10^{-5}$, $7.8 \times 10^{-6}$, $3.9 \times 10^{-6}$, $2.0 \times 10^{-6}$, $9.8 \times 10^{-7}$, $4.9 \times 10^{-7}$, $2.4 \times 10^{-7}$, $1.2 \times 10^{-7}$, $6.1 \times 10^{-8}$, and 0 M. A total of 150 $\mu$L of each GD dilution was prepared. 100 $\mu$L aliquots of each dilution were applied to each of sixteen prepared spin columns as per the manufacturer's directions. The columns were centrifuged at 1000× g for 2 minutes and the effluent was collected. Next, 20 $\mu$L of each GD solution's effluent as well as 20 $\mu$L of each GD dilution was applied to a microtiter plate. 100 $\mu$L aliquots of human whole blood were applied to each of the 32 microtiter wells followed by thorough mixing. After incubation at room temperature for 2 hours, the concentration of AChE and BChE contained within each sample was determined as described in Example 2. FIGS. 6A and 6B show graphs which demonstrate that the spin columns are capable of removing up to 100 nmol (i.e., 100 $\mu$L of $1.0 \times 10^{-3}$ M) of a small organic molecule such as GD.

B. Thoroughly Lysed Whole Blood Applied to Biorad P6 Spin Columns

Figure 6C:
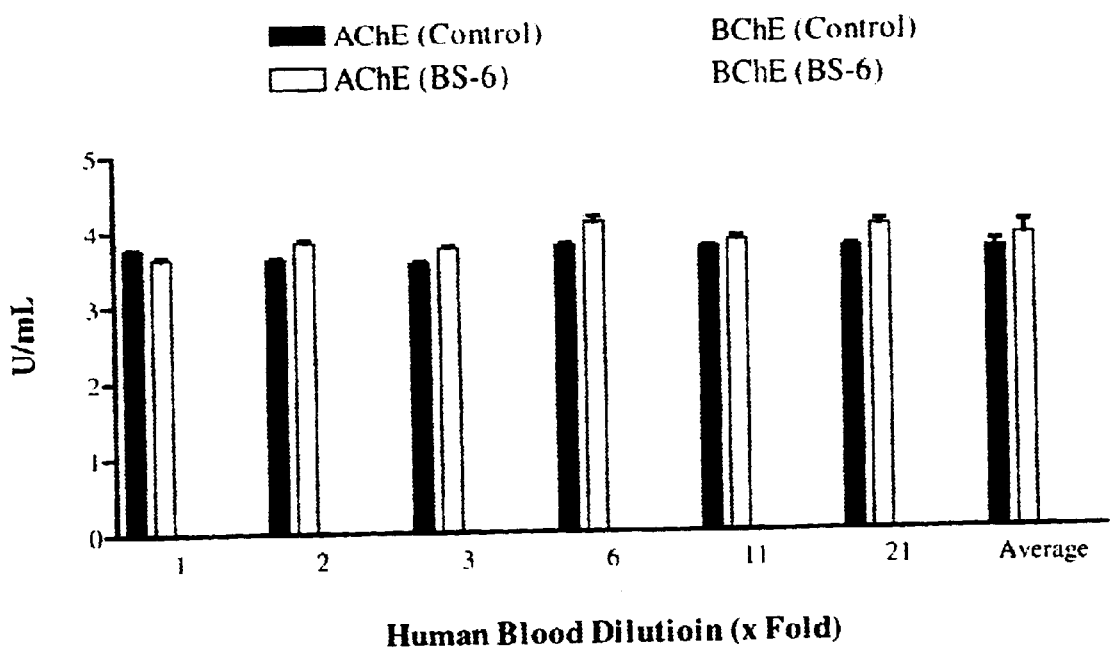
FIG. 6C illustrates that spin columns do not retain the AChE and BChE contained in thoroughly hemolysed whole blood samples.

Four month old human blood test samples, thoroughly hemolyzed, were diluted with water and resulted in blood concentrations of 1.0, 0.545, 0.298, 0.162, 0.089, and 0.048 (volume: volume). A 100 $\mu$L aliquot of each test sample was added to a prepared spin column as per the manufacture's directions. The columns were centrifuged for 2 minutes at 1000× g. The cholinesterase assay as described in Example 2 was performed on each column effluent and a fraction of the blood remaining in each original matched test sample. The cholinesterase levels contained in each sample were plotted and are depicted in FIG. 6C. Thus, cholinesterase from thoroughly hemolyzed human whole blood samples was not retained by the Biorad P6 spin columns.

FIGS. 6A, 6B, and 6C demonstrate that the spin column method effectively removes GD and that AChE and BChE contained in thoroughly hemolyzed whole blood samples are not retained on Biorad P6 spin columns. Thus, small interfering compounds such as oximes can easily be removed from test samples, such as blood samples, by this method.

C. Removal of Free Uncomplexed PB via Biorad P6 Spin Columns

Figure 6D:
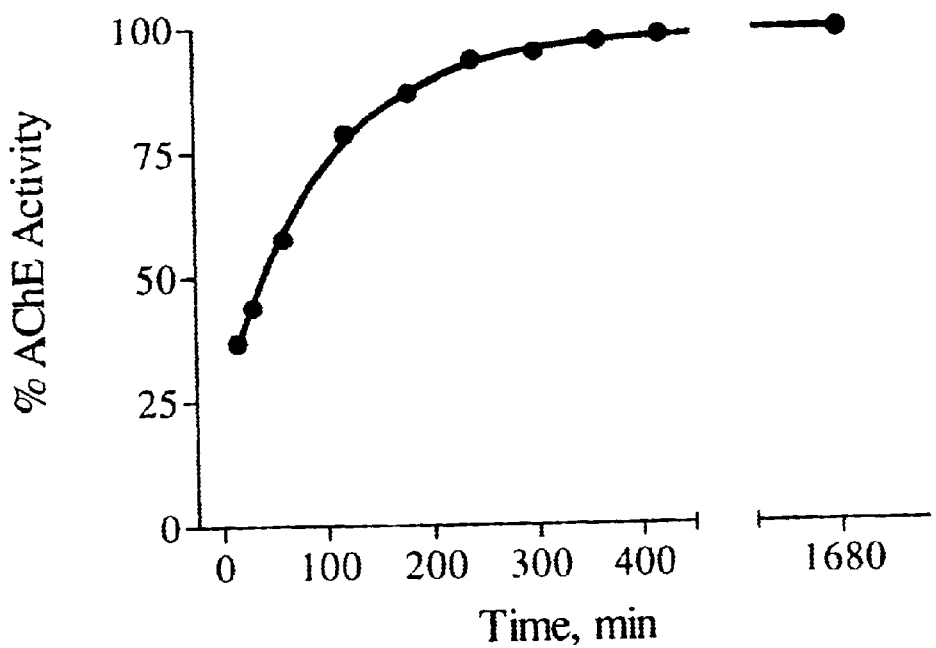
FIG. 6D demonstrates that spin column chromatography effectively removed free unbound pyridostigmine bromide from a complex matrix of human blood.

One hundred fifty microliters of human blood was treated with enough PB to achieve about 75% inhibition of AChE at the end of a thirty minute incubation at room temperature. A control sample was treated with an equal volume of water. These samples were prepared as is common in the art. After incubation, a 100 microliter fraction of each test blood sample were applied to separate Biorad P6 spin columns prepared as per the manufacture's directions. Both columns, one containing the PB inhibited blood the other containing the matched control, were centrifuged at 1000× g for two minutes. After centrifugation, the cholinesterase activity of each effluent was monitored at 15, 30, 60, 120, 180, 240, 300, 360, 420, and 1680 minutes post column. The results are depicted in FIG. 6D as the ratio of the inhibited to control activity as a function of time. FIG. 6D illustrates that spin column separation can be used to separate uncomplexed ligands from a complex sample matrix such as blood. Without spin column chromatography, the return to normal activity would not have occurred during the monitored time frame. See FIG. 4 for a similar example without size exclusion chromatography.

Thus, spin column chromatography can be used to quickly and efficiently remove small interfering compounds from test samples such as blood without retaining cholinesterase within the column's matrix.

EXAMPLE 9

Comparison with COBAS/FARA and Test-Mate OP™ Methods

The cholinesterase assay of the present invention as described in Example 2 was compared with a standard clinical assay, COBAS/FARA (Roche Diagnostics Corporation, Indianapolis, Ind.), and the accepted field assay of the United States Army, the TestMate OP method, technical bulletin 296.

A vial of dilute GD, 10 mM in saline, was stored frozen until further dilutions were prepared. 200 $\mu$L of saline was added to a microtube and set aside. The GD was thawed and two dilutions were prepared to achieve a target dilution of 1 $\mu$M. 200 $\mu$L of the 1 $\mu$M GD in saline was pipetted into a microtube and set aside. Then, serial dilutions were prepared and resulted in concentrations of 1000, 800, 640, 512, 410, 328, 262, 210, 168, 134, 107, 86, 69, 0 nM of GD. Fresh human whole blood was collected from ten subjects by a phlebotomist in heparin Vacutainer®.

Next, 200 $\mu$L aliquots of each GD concentration were transferred to 1.5 mL microfuge tubes. This was repeated 10 times, one for each human subject, at each GD concentration (i.e., a total of 140 microfuge tubes or 10 sets of 14 GD concentrations). To each of the 14 tubes within the GD sample set, one milliliter of a particular subject's blood was added with a positive displacement pipettor. The tubes were capped and mixed by inversion. This process was repeated for the remaining nine human subject blood test samples. All 140 test samples were incubated overnight at room temperature, and then the cholinesterase assay as described in Example 2 was performed.

A fraction of the remaining test samples were analyzed for AChE and BChE content using the procedure of the Test-Mate Op™ system as per the manufacturer's directions. The remainder of each test sample was centrifuged for 5 minutes at 14,000 RPM. Plasma from each tube was carefully removed and placed into appropriately labeled microtubes for cholinesterase analysis. The remaining red blood cells (RBCs) in each tube were mixed and diluted 50 fold by placing 20 $\mu$L of RBCs into microtubes containing 980 $\mu$L of 1% Triton X-100 in saline. The plasma was diluted 15 fold by placing 68 $\mu$L plasma into microtubes containing 932 $\mu$L of 1% Triton X-100 in saline. Then the COBAS/FARA assay was performed. Each blood test sample was analyzed in triplicate with each specific cholinesterase assay. In other words, the test samples were analyzed 3× for erythrocyte (AChE) and plasma (BChE) cholinesterase activity.

Figure 7A:
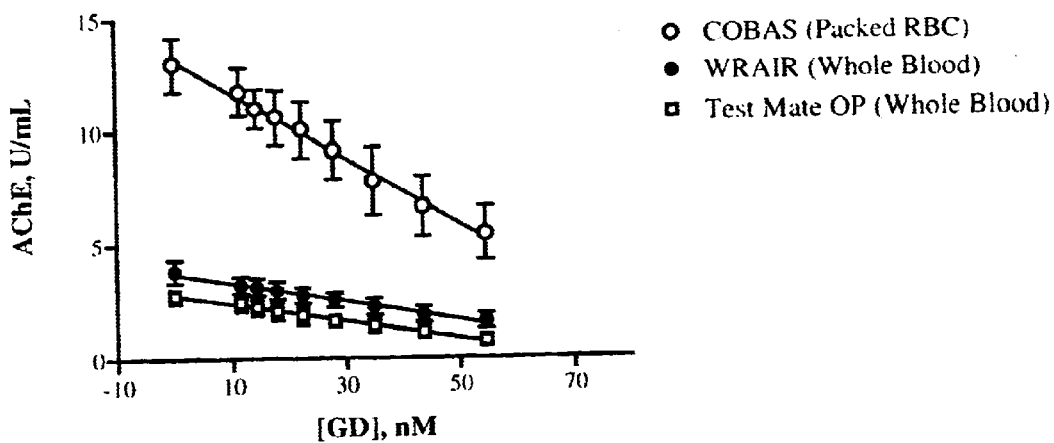
FIG. 7A shows a graph, which illustrates that the cholinesterase assay of the present invention, the COBAS/FARA, and the TestMate OP methods produce colinear titrations for an average population for human AChE.

The average concentrations of AChE as determined by the cholinesterase assay of Example 2 were 3.88, 3.25, 3.15, 2.98, 2.75, 2.55, 2.23, 1.87, 1.58, 1.11, 0.64, 0.36, 0.13, and 0.04 U/mL for each serial dilution, respectively. The average concentrations of AChE as determined by the COBAS/FARA assay were 12.97, 11.73, 10.99, 10.61, 10.07, 9.14, 7.80, 6.69, 5.47, 4.01, 2.46, 1.58, 0.61, and 0.34 U/mL for each serial dilution, respectively. The concentrations of AChE as determined by the Test-Mate OP™ method were 2.74, 2.43, 2.23, 2.05, 1.85, 1.61, 1.41, 1.12, 0.75, 0.41, 0.15, 0.04, 0.00, and 0.00 U/mL for each serial dilution, respectively. These concentrations were plotted as shown in FIG. 7A. In FIG. 7A, it is important to note that for clarity only the linear titration range is depicted.

Figure 7B:
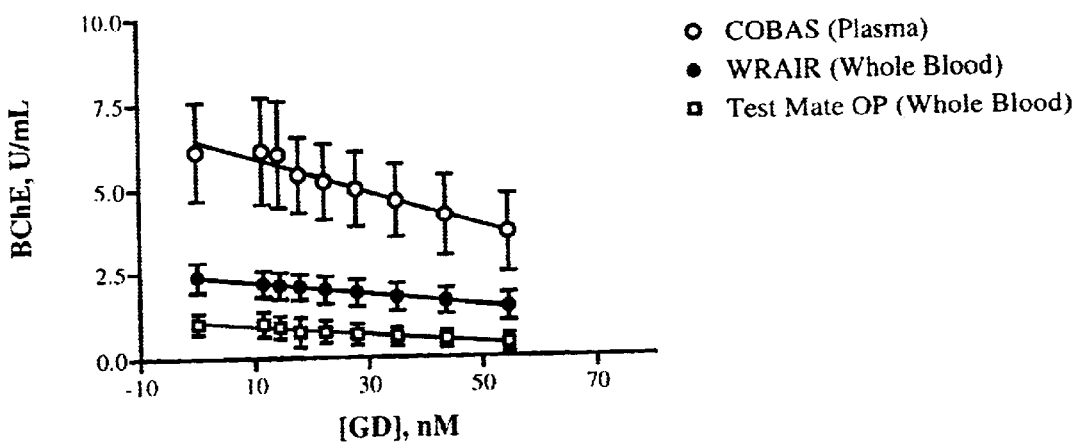
FIG. 7B shows a graph, which illustrates that the cholinesterase assay of the present invention, the COBAS/FARA, and the TestMate OP methods produce colinear titrations for an average population for human BChE.

The average concentrations of BChE as determined by the cholinesterase assay of Example 2 were 2.38, 2.17, 2.12, 2.07, 1.99, 1.90, 1.77, 1.65, 1.47, 1.28, 0.95, 0.71, 0.35, and 0.14 U/mL each serial dilution, respectively. The average concentrations of BChE as determined by the COBAS/FARA assay were 6.12, 6.13, 6.02, 5.41, 5.21, 4.98, 4.63, 4.19, 3.67, 3.06, 2.29, 1.61, 0.75, and 0.20 U/mL for each serial dilution, respectively. The concentrations of BChE as determined by the Test-Mate OP™ method were 1.02, 1.00, 0.90, 0.75, 0.76, 0.68, 0.60, 0.52, 0.41, 0.31, 0.14, 0.06, 0.00, and 0.00 U/mL for each serial dilution, respectively. These concentrations were plotted as shown in FIG. 7B. In FIG. 7B, it is important to note that for clarity only the linear titration range is depicted.

Figure 7C:
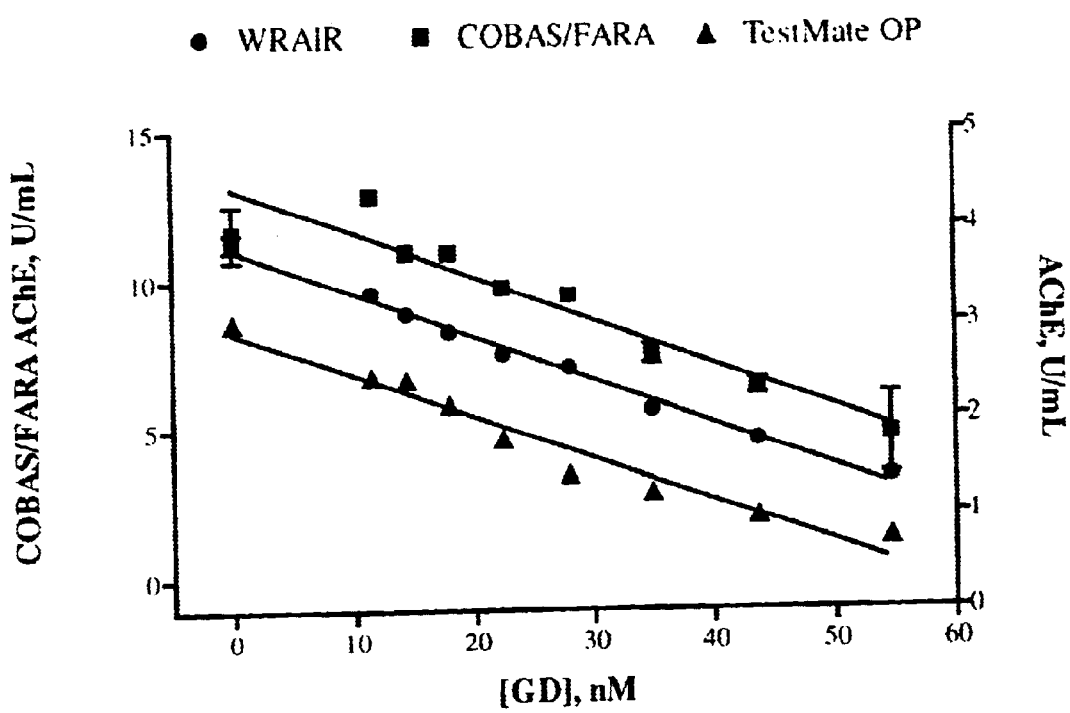
FIG. 7C shows a graph, which illustrates that for any given individual the cholinesterase assay of the current invention produces results for human AChE that are more colinear than the COBAS/FARA or TestMate OP methods.

FIGS. 7A and 7B clearly demonstrate that all three methods produce co-linear trends for both AChE and BChE, however, the depicted figures are a reflection of the average population. Therefore, large sample numbers can mask significant individual deviations. This is illustrated in FIG. 7C for the Test-Mate Op™ and the COBAS/FARA methods. In fact, for any given individual sample, the results determined by the methodology of this invention are more co-linear than those of the other two techniques and therefore more reliable and accurate. FIGS. 7A and 7B also illustrate that the cholinesterase assay of the present invention produces titrations that are more tightly distributed around the mean than the COBAS/FARA or Test-Mate OP™ assays. The average population distributions for the COBAS/FARA, Test-Mate Op™, and the current invention are 13%, 12%, and 9%, respectively for AChE and 24%, 30%, and 19%, respectively for BChE.

Figure 7D:
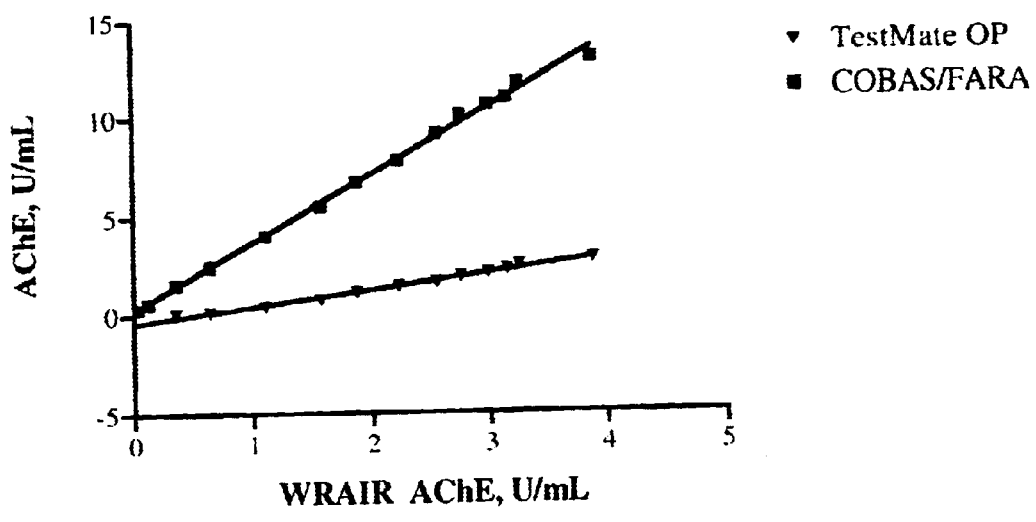
FIG. 7D is a graph showing that the concentrations of human AChE obtained with the COBAS/FARA and TestMate OP methods can be converted to those of the current invention by the use of a simple linear function.
Figure 7E:
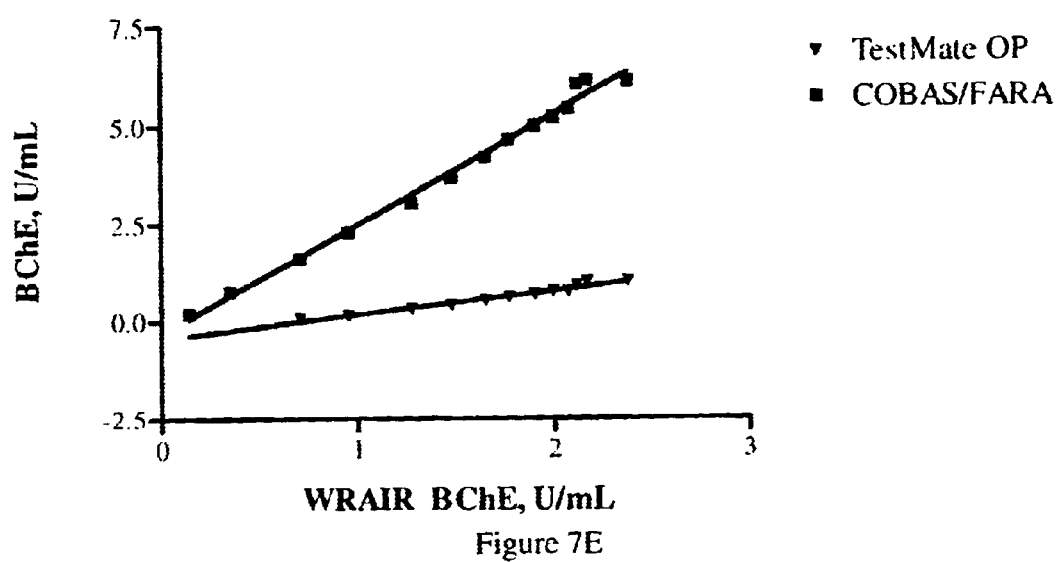
FIG. 7E is a graph showing that the concentrations of human BChE obtained with the COBAS/FARA and Test- Mate OP methods can be converted to those of the current invention by the use of a simple linear function.

Since each absolute value for AChE and BChE are different for each assay conducted, the average results obtained from the COBAS/FARA and Test-Mate OP™ methods were plotted as a function of the average AChE/BChE concentration determined from Example 2. FIGS. 7D and 7E clearly demonstrate the linear relationship between the two established assay methods and that of the current invention for both AChE and BChE. FIGS. 7D and 7E also demonstrate that results from established methods can be converted to those of the current invention by applying a simple linear transformation. This allows the conversion of cholinesterase databases constructed using prior methods to be converted to the values of the current invention once validation between the methods has been established.

EXAMPLE 10

In-Vivo Monitoring

The cholinesterase assay of the present invention as described in Example 2 was used to assess the extent of AChE and BChE inhibition in Hartley guinea pigs induced by intramuscular (IM) injection of pyridostigmine bromide (PB) (Sigma, St. Louis, Mo.) as a function of time. The experiment was repeated several times at various PB doses to determine the peak inhibition time and the extent of AChE inhibition as a function of IM PB dose.

Specifically each experiment consisted of the following. Stock solutions of PB were prepared in saline such that an injection of a 100 $\mu$L aliquot of said solution IM into an adult male Hartley guinea pig of a known weight produced doses of 5, 10, 20, and 40 µg/kg body weight PB. At time 0, 100 µL of a particular PB stock solution was injected IM into an adult male Hartley guinea pig of a predetermined weight achieving the desired PB dose. At times 0, 15, 30, 60, 90, 120, 150, 180, 240 and 300 minutes the guinea pig was bled through an implanted carotid artery catheter. At the specified time, the catheter was opened and two drops of blood were discarded. This blood represented the void volume of the catheter. 20 µL of the next drop of blood was collected and transferred to a 200 µL PCR tube containing 8 U of heparin (8 µL of 1000 U/mL heparin, VWR Scientific, Bridgeport, N.J.). Following thorough mixing, the blood samples were flash frozen on powdered dry ice and stored at −80° C. until the completion of the experiment.

At the end of each experiment, all of the samples were batch analyzed for AChE and BChE concentration and activity as described in Example 2. However, a slight modification of Example 2 was used in that 132 µL instead of 140 µL of 18.2 MΩ water was added to each frozen blood sample. The overall dilution due to sample preparation, however, was still 8 fold (i.e., 20 µL blood in a total volume of 160 µL).

Figure 8A:
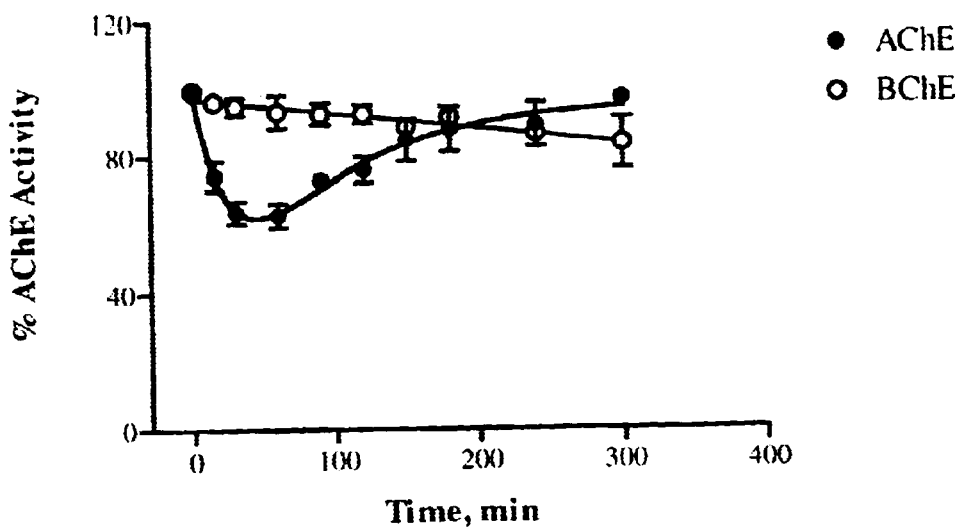
FIG. 8A shows a graph illustrating the pharmacokinetics as reflected in the AChE and BChE concentrations for Harley guinea pigs injected intramuscularly with 20 $\mu$g/kg body weight of pyridostigmine bromide.
Figure 8B:
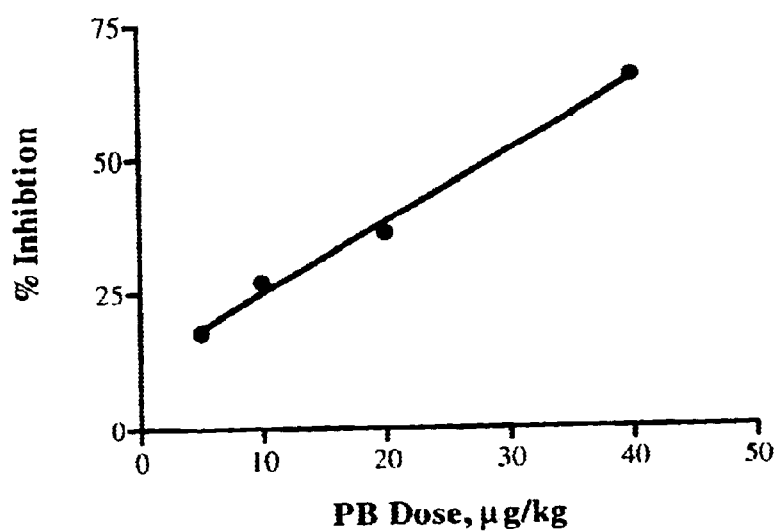
FIG. 8B shows a graph illustrating the dose dependent in-vivo peak inhibition of pyridostigmine bromide for Hartley guinea pigs.

All data was normalized to percent control activity by dividing the AChE and BChE concentrations by those determined at time 0. The percent activity data sets for a given PB dose were averaged together for each time point and the standard deviations for each time point was also calculated. The average AChE and BChE activities as a function of time were plotted and fit to standard equations known in the art. FIG. 8A represents the average data set for the 20 µg/kg dose. Using standard equations known in the art, the peak inhibition time for the PB dose range investigated was determined to be about 30 minutes. Therefore, the extent of inhibition at 30 minutes was calculated from the theoretical fits to determine peak inhibition. Peak inhibition was plotted as a function of PB dose and is depicted in FIG. 8B.

This experiment demonstrates that the assay of the current invention is capable of monitoring the pharmacokinetics and pharmacodynamics of in-vivo administered compounds that affect the concentration or activities of AChE, BChE, or both. Therefore, due to the unique characteristics of the method of this invention, it can easily be extended to any other in-vivo experiment designed to monitor the concentrations or activities of AChE, BChE, or both in whole blood or any other biological tissue, fluid, or sample containing AChE, BChE, or both. In addition, the assay set forth in this invention can be used to monitor the progress of a treatment regime, since periodic monitoring of the concentrations of AChE, BChE, or both as a function of time would be required. This parallels the time course nature of this in-vivo experiment.

EXAMPLE 11

Monitoring the Stability of AChE and BChE in a Whole Blood

The cholinesterase assay of the present invention as described in Example 2 was used to monitor the stability of whole blood AChE and BChE to extreme freezing. The goal of this experiment was to determine if Hartley guinea pig whole blood could be stored at −80° C. for prolonged periods of time without altering the cholinesterase activity. In addition, the effect of repetitive freeze thawing on dry ice was also investigated. These two issues are of great concern for batch sample processing of time sensitive samples.

A. Prolonged exposure to −80° C.

Figure 9A:
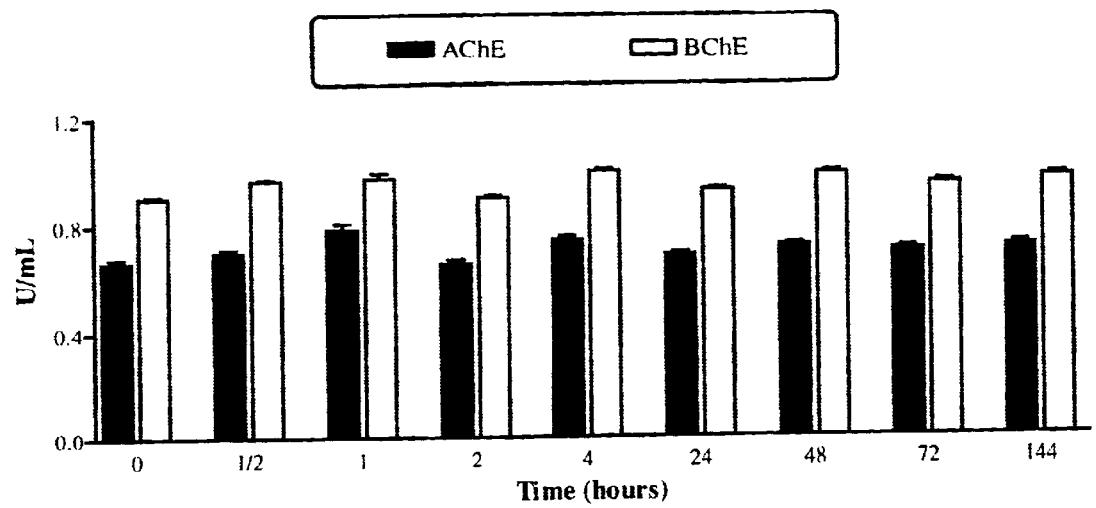
FIG. 9A depicts the response of the AChE and BChE concentration/activity of Hartley guinea pig blood to prolonged exposure at $-80°$ C.

Eight 20 µL aliquots of heparin treated Guinea pig whole blood were added to eight 200 µL PCR tubes. Seven of these were flash frozen on powdered dry ice then stored at −80° C. The eighth sample was marked as time zero, and analyzed for cholinesterase content as per example 2. At times 0.5, 1, 2, 4, 24, 48, 72, and 144 hours, one of the PCR tubes was removed from the deep freezer and assayed for cholinesterase content again as described in Example 2. The AChE and BChE levels were plotted as a function of time frozen, and the results are depicted in FIG. 9A.

This experiment clearly illustrates that prolonged exposure to harsh temperatures does not alter the activities or concentrations or AChE or BChE contained in guinea pig whole blood. The average AChE and BChE concentrations for this experiment were 0.71±0.04 U/mL and 0.96±0.04 U/mL, respectively, while the respective control values were 0.72±0.01 U/mL and 0.97±0.01 U/mL.

B. Repetitive Freeze Thawing

Figure 9B:
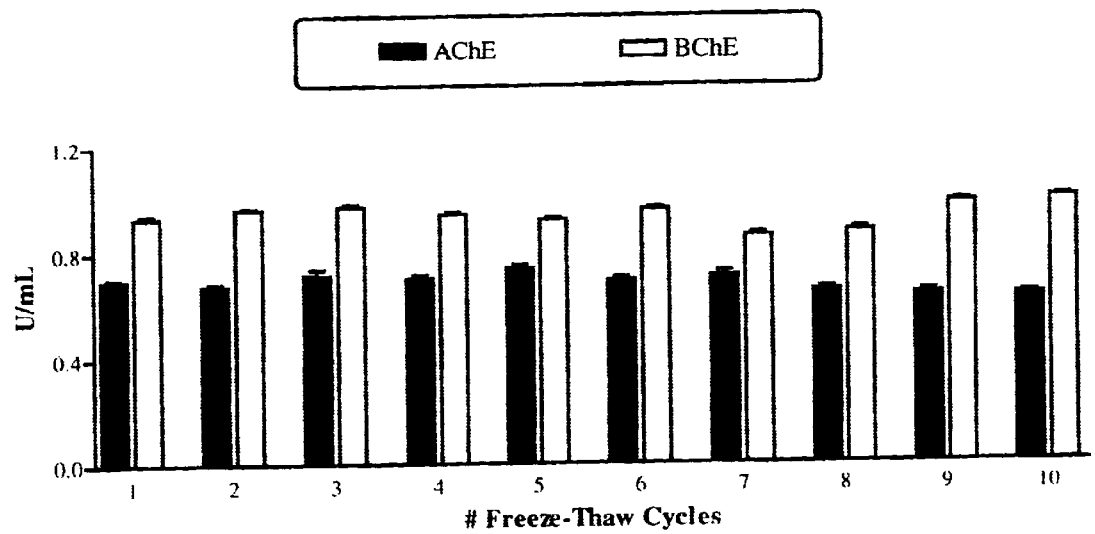
FIG. 9B depicts the effect of repetitive freeze-thawing on the concentrations of AChE and BChE contained in Hartley guinea pig whole blood.

A 450 µL aliquot of heparin treated Hartley guinea pig whole blood was frozen over dry ice and repeatedly frozen then thawed. During each thawing, a 20 µL aliquot was diluted to a final volume of 160 µL using 18.2 MΩ water. Each sample was then assayed as described in Example 2 for the concentrations and activities of AChE and BChE. The results were then plotted as a function of the number of times frozen then thawed. The results are depicted in FIG. 9B. As is clearly demonstrated by FIG. 9B, repetitive freezing does not alter guinea pig blood cholinesterase content. The average AChE and BChE concentrations for this experiment were 0.68±0.04 U/mL and 0.94±0.04 U/mL, respectively, while the respective control values were 0.630±0.008 U/mL and 0.994±0.006 U/mL. This fact when compared to A above allows even greater flexibility in experimental design and sample storage for subsequent batch analysis.

As demonstrated by the previous two examples, the method as detailed in the invention is capable of monitoring the stability of a biological sample. In addition, this method could be extended to any other sample containing AChE, BChE, or both in order to assess sample stability or the effect a particular processing step causes on the stability of the proteins in a sample.

Example 12

Validation of Automated Cholinesterase Assay

Figure 12:
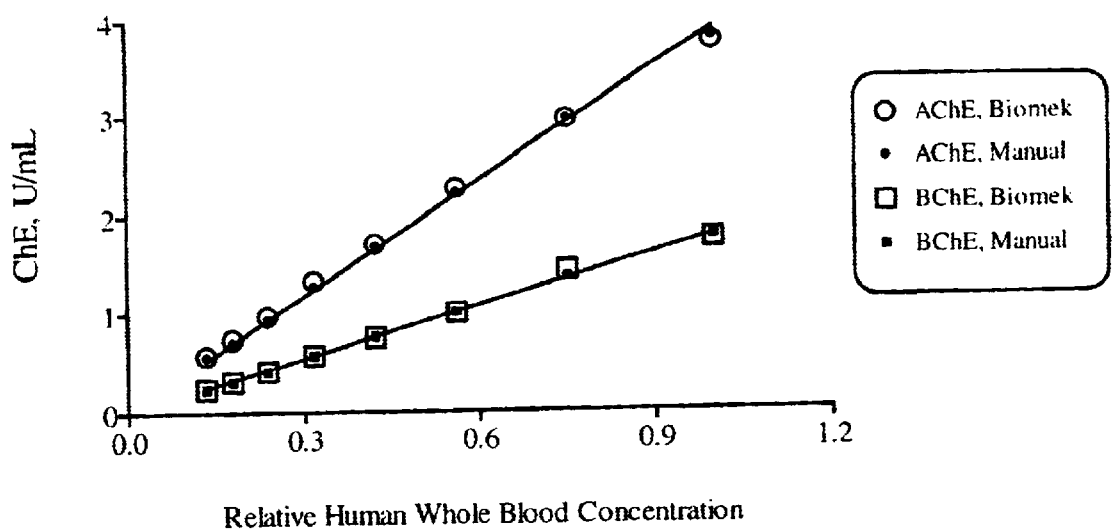
FIG. 12 demonstrates that automation of the assay of the present invention yielded substantially similar results to that of the manual method detailed in Example 2 below.

The cholinesterase assay of the current invention as set forth in Example 2 was ported to an automated platform. This was accomplished by interfacing a Molecular Devices SpectraMax Plus to a Beckman-Coulter Biomek 2000 liquid handling workstation. The Biomek 2000 was then programmed to perform all of the necessary plate handling, sample preparation, and reagent additions as described in Example 2. To demonstrate that the manual and automated methods produced comparable results, the cholinesterase levels of a series of serial dilutions of human whole blood were measured via Example 2 and the Biomek 2000 ported method described above. The serial dilutions were prepared in 18.2 MΩ water and included relative blood concentrations of 1.0 (undiluted whole blood), 0.75, 0.56, 0.42, 0.32, 0.24, 0.18, and 0.13. The AChE and BChE activities were plotted as a function of relative blood concentration for both methods and are depicted in FIG. 12. The AChE slopes determed via linear least squares analysis were 3.91±0.05 and 3.90±0.02 U/mL/blood dilution for the Biomek 2000 and manual methods, respectively. The similarly determined slopes for BChE were 1.80±0.02 and 1.79±0.01 U/mL/blood dilution for the Biomek 2000 and manual methods, respectively. As shown by the slopes and FIG. 12, essentially no bias was introduced by porting the method to the Biomek 2000 platform as comparable results were obtained.

EXAMPLE 13

Inter-lab Validation

Figure 13:
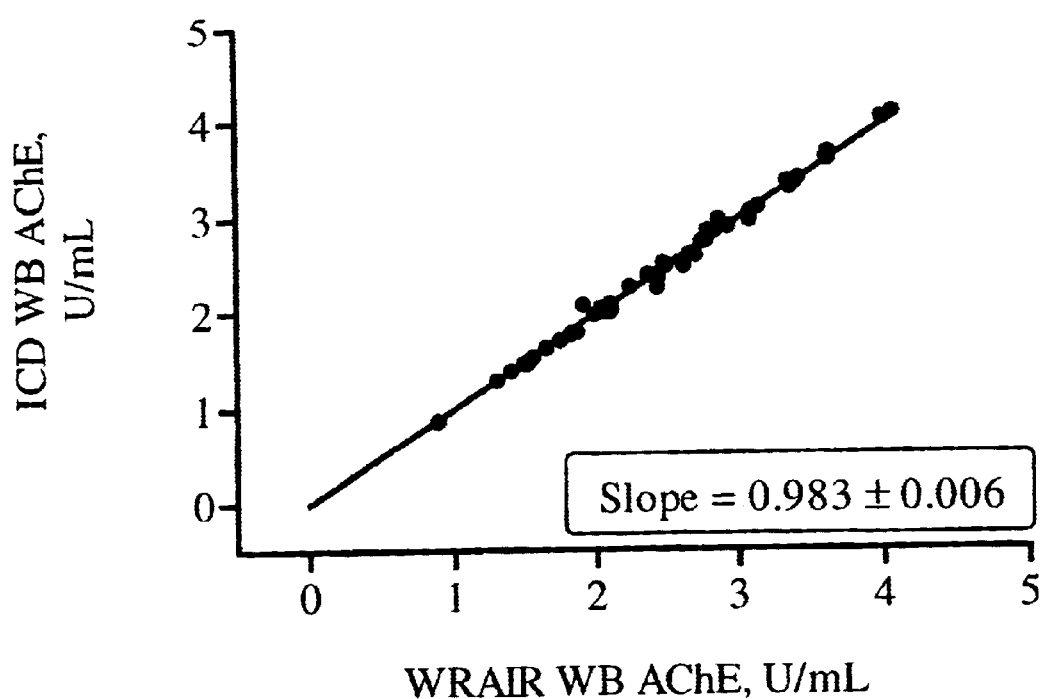
FIG. 13 shows that the assay of the present invention can be ported to other laboratories without introducing a bias in the sample results.

The automated cholinesterase assay of the present invention as described in Example 12 was implemented at the United States Army Medical Research Institute of Chemical Defense (USAMRICD) as well as the Walter Reed Army Institute of Research (WRAIR). To validate the assay, each lab independently prepared all stock reagents as detailed in Example 2. Next, blood samples from eight human volunteers were titrated ex vivo with six different doses of GD to produce cholinesterase inhibition ranging from about 0% to about 75% inhibition by standard methods in the art. After an overnight incubation, both labs independently measured the AChE activity for each sample. The results were graphed as "ICD AChE" versus "WRAIR AChE". See FIG. 13. Linear least squares analysis of the data produced a slope of 0.983±0.006. The slope indicates that less than about a 1.7% bias exists between the two institutes which is most likely due to inter run variability since it is less than the inter run variability of about 1.9% for human blood reported in Example 2. Finally, this example illustrates that the assay of the current invention is easily ported to other facilities.

EXAMPLE 14

Comparable Results for Whole Blood and Packed Red Blood Cells

To demonstrate the assay of the current invention produces comparable results for both whole blood and packed red blood cells, fresh blood from eight human volunteers was titrated ex vivo with six different doses of GD to produce cholinesterase inhibition ranging from about 0% to about 75% inhibition by methods standard in the art. Roughly half of the sample was centrifuged in order to separate the RBCs from the plasma by methods standard in the art. After an overnight incubation, all samples were independently assayed for AChE activity. Data processing included population normalization as explained in Example 2.

Figure 14:
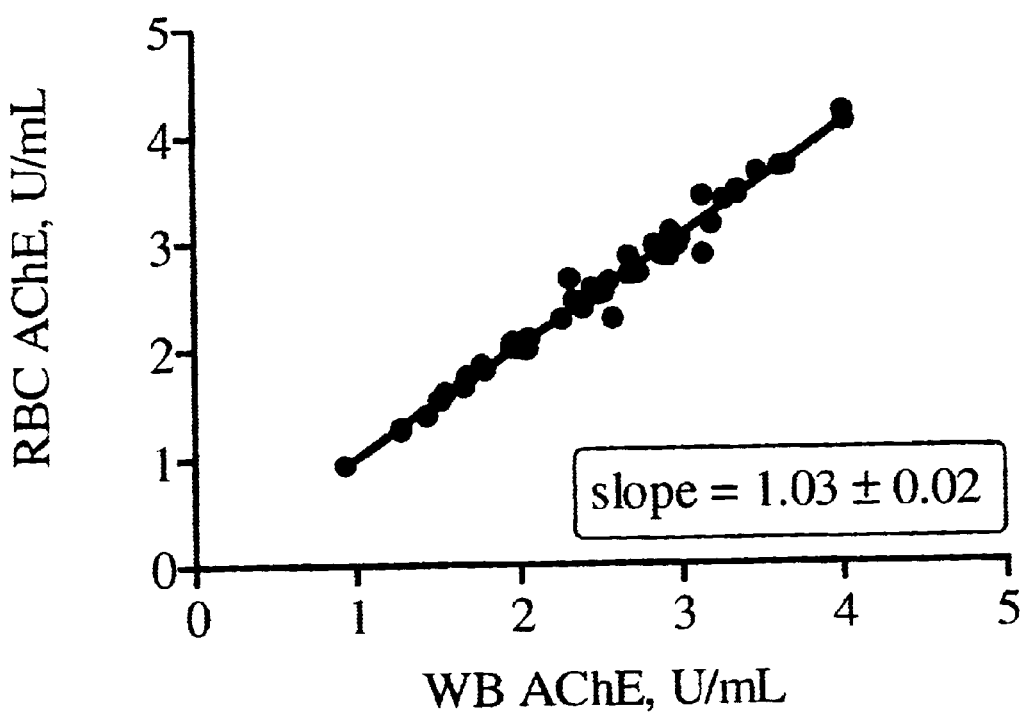
FIG. 14 is a plot of packed red blood cell (RBC) AChE activity as a function of their parent whole blood (WB) values as determined by the assay of the present invention.

The results were graphed as "RBC AChE" versus "WB AChE" as shown in FIG. 14 which is a plot of packed red blood cell (RBC) AChE activity as a function of their parent whole blood (WB) values as determined by the assay of the present invention. FIG. 14 illustrates that that the assay produces the substantially the same results for both RBC and WB samples. This is unlike other assays known in the art. The range of cholinesterase levels was achieved by titrating human whole blood with the nerve agent GD as is common in the art. Linear least squares analysis of the data produced a slope of 1.03±0.02. The slope indicates that less than about a 3% bias exists between the two institutes which is most likely due to inter run variability since it is about the same magnitude as that for the inter run variability of about 1.9% for human blood reported in Example 2.

EXAMPLE 15

Equality of Intravenous and Finger Prick Methods of Sample Collection

Figure 15A:
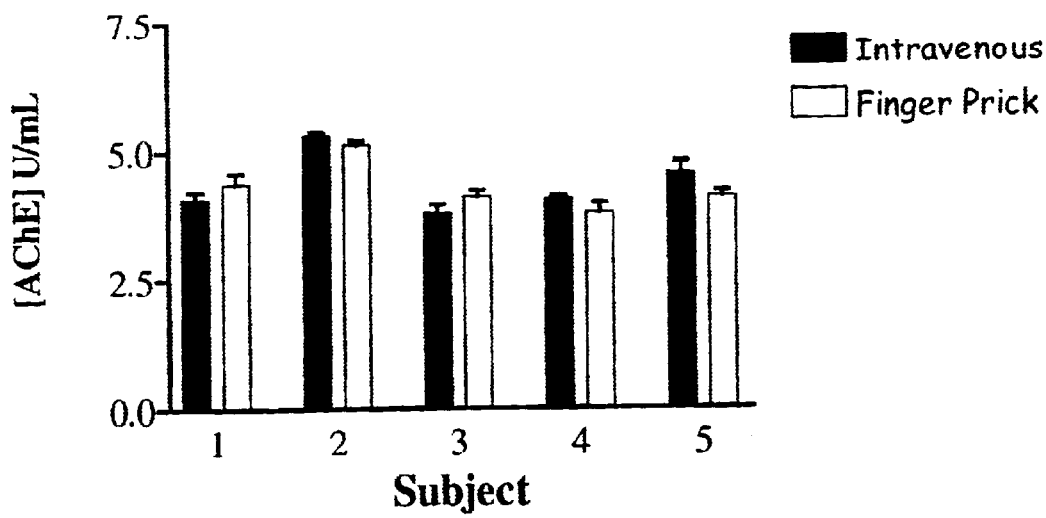
FIG. 15 depicts that substantially the same AChE (Panel A) and BChE (Panel B) activities are derived for human whole blood samples obtained from either an intravenous draw or a finger prick sampling.
Figure 15B:
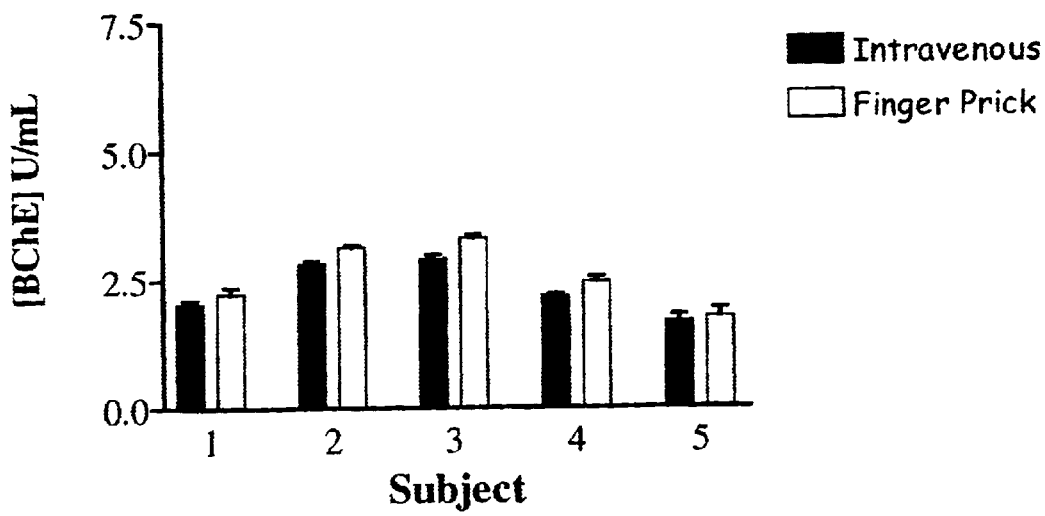

To determine if sample collection produced different results, blood was collected intravenously, Iv blood, by a phlebotomist using heparin-coated vacutainers by methods standard in the art. At the same time, ten microliters of blood was collected with a positive displacement pipette from a lancet finger prick, FP blood, of the same five individuals. The FP blood was immediately diluted 20 fold with 18.2 MΩ water. The AChE and BChE activities were measured as per Example 2, except that the FP blood sample was already considered processed. The results were plotted as individual bar charts for AChE and BChE. See FIG. 15. The average AChE activity for the five volunteers was about 4.3±0.6 and about 4.3±0.5 for the IV blood and FP blood samples, respectively. The average BChE activity for the five volunteers was about 2.3±0.5 and about 2.6±0.6 for the IV blood and FP blood samples, respectively. Thus, different blood sources, IV blood or IP blood, provides comparable results for the cholinesterase activity determined by Example 2.

EXAMPLE 16

Inter and Intra Day Assay Variability

Figure 16A:
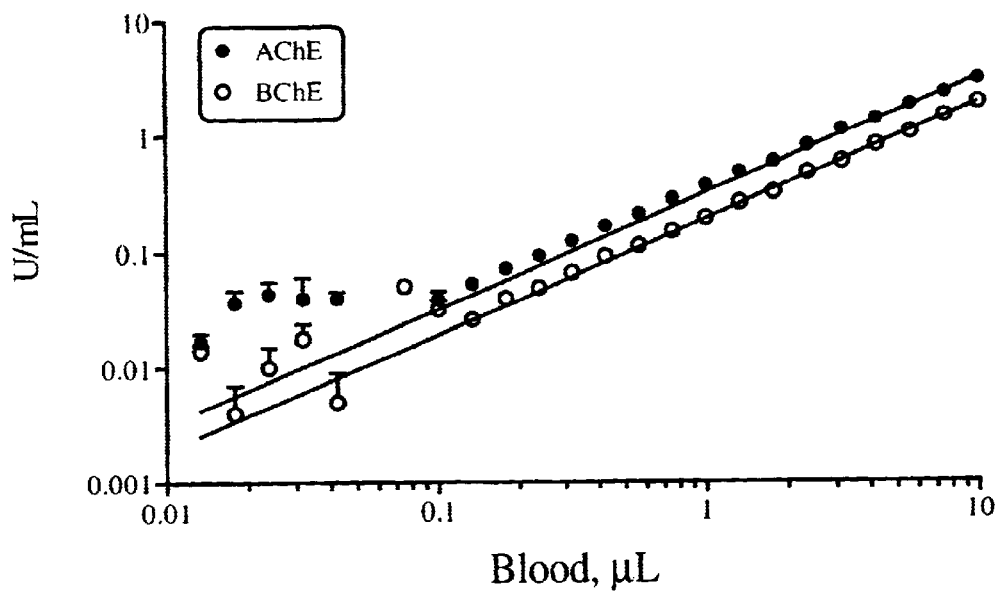
FIG. 16 demonstrates that the assay of the present invention provides substantially the same results when performed six times during one day or once over three successive days. Panel A depicts a single runs data and demonstrates that the assay is linear over nearly two orders of magnitude. Panel B displays the processed inter and intra day variability.
Figure 16B:
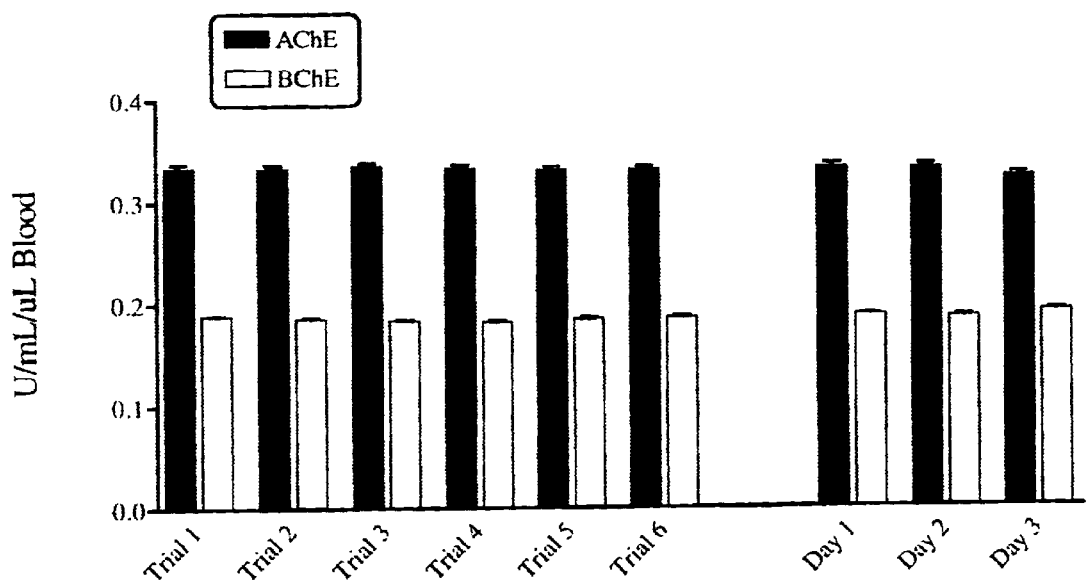

To determine the inter and intra day variability of the present invention of Example 2 as implemented on the Biomek 2000 system detailed previously, fresh human whole blood was diluted serially with 18.2 MΩ water. Next, the cholinesterase levels of each blood dilution was determined as explained in Example 2 as implemented on the Biomek 2000 workstation. This was repeated six times on one day, and then once a day for three consecutive days. The AChE and BChE values were plotted as a function of blood volume followed by linear least squares analysis of only the linear portion of each data set. See FIG. 16A for a representative plot. Next, the slopes from each trial were plotted as a bar graph for both the inter and intra day data. See FIG. 16B. The % CV for the six intraday runs was about 0.5% and about 1.1% for AChE and BChE, respectively. While the % CV for the three interday determinations was about 1.7% and about 1.5% for AChE and BChE, respectively. These results show that the present invention provides the determination of highly precise cholinesterase values. Additionally, FIG. 16A demonstrates that the assay of the present invention is linear over about two orders of magnitude that translates into a linear range of detection of about 0% to about 99% which is consistent with that previously reported in Example 2.

EXAMPLE 17

Robustness of the Assay with Respect to Substrate Concentration

To determine the effect of substrate variation on the assay of the current invention as implemented on a Biomek 2000 liquid handling workstation, human whole blood sample serial dilutions were assayed in the presence of various concentrations of each substrate (i.e., ATC, PTC, BTC). The concentration of each substrate was independently varied from about 20% below normal to about 20% above normal in 10% increments. Normal is defined as the concentration of the stock solutions as in Example 2. This resulted in a matrix comprising 125 different combinations of ATC, PTC, and BTC (i.e., 5 ATC levels (−20%, −10%, normal, 10%, 20%)×5 PTC levels×5 BTC levels=125).

Each of the 125 elements of the substrate matrix was used to determine the AChE and BChE levels in each of the eight serial blood dilutions. The AChE and BChE results were plotted as a function of blood dilution, and the slopes of the resulting linear relationships were determined via linear least squares analysis. The slopes for AChE and BChE were normalized to that of the normal method (i.e., substantially the same conditions of Example 2). The 125 normalized values produced an average of about 100±5% and about 103±7% for AChE and BChE, respectively. These results show that the assay of Example 2 is extremely robust with respect to substrate variation since about a 40% swing in any individual substrate produced no statistically observable deviation in the calculate cholinesterase activities.

EXAMPLE 18

Percent AChE Lost During Blood Donation

Figure 17:
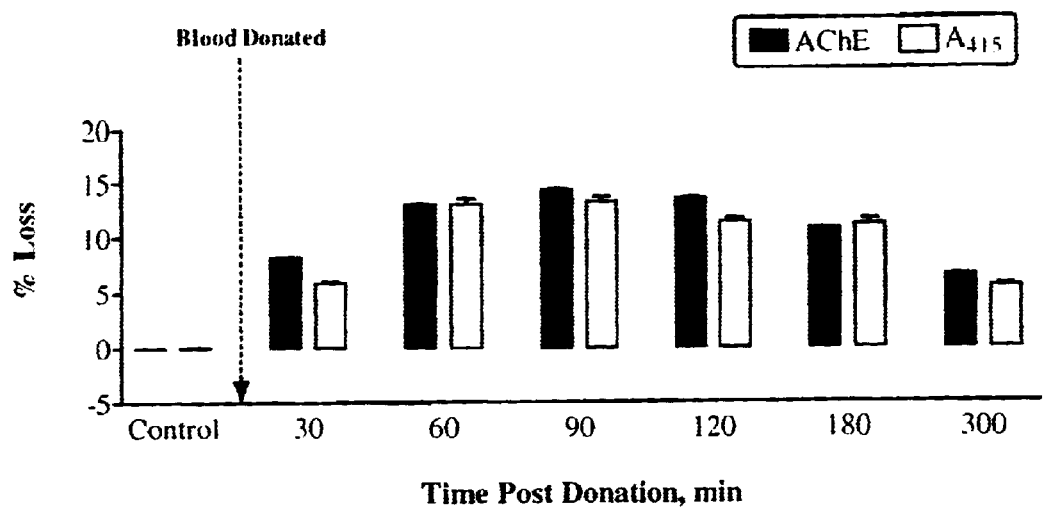
FIG. 17 demonstrates that the assay of the current invention is highly sensitive as changes in activity of about 1.5% are readily apparent.

The assay of the present invention was used to screen an individual for loss in AChE activity as a function of time due to blood donation. In this experiment, a volunteer donated one unit of whole blood. Blood AChE levels and the blood sample's absorbance at 415 nm, $A_{415}$, were measured as per Example 2 at 30 minutes prior to donation and at 30, 60, 90, 120, 180, and 300 minutes post donation. The percent loss in AChE activity and $A_{415}$ were calculated based on the 30 minute pre-donation levels. The results were graphed and are depicted in FIG. 17. FIG. 17 shows the percent loss in human AChE activity following donation of one standard unit of blood as well as the loss in hemoglobin as reflected by the decrease in the absorbance at 415 nm ($A_{415}$). FIG. 17 illustrates two important points. First, the loss of AChE activity tracks identically to the loss in $A_{415}$ which is a crude measure of hematocrit since hemoglobin, a normal component of RBCs, absorbs maximally at 415 nm. Second, the assay of Example 2 is capable of measuring minute changes in AChE activity, about 1.5%. Thus, this assay may be used to monitor subtle changes, about 1.5%, in AChE levels such as subtle changes resulting from pesticide poisoning, blood loss during surgery, or the like.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. An assay for detecting, measuring or monitoring the activity or concentration of a protein in a test sample, wherein the protein belongs to a plurality of proteins and the plurality of proteins have similar or overlapping properties towards a plurality of substrates, comprising adding the plurality of substrates to a plurality of aliquots of the test sample;

measuring reaction rates between the protein and each substrate;

determining the activity or the concentration of the protein in the test sample with using a sensitivity coefficient for each substrate and for each protein, wherein the sensitivity coefficient was determined from a sensitivity coefficient sample by obtaining a plurality of inhibited dilutions of the sensitivity coefficient sample, wherein the plurality of inhibited dilutions comprise a plurality of concentrations of the protein which are partially to completely inhibited;

exposing each inhibited dilution of the plurality of inhibited dilutions to each substrate;

measuring the reaction rates between each uninhibited protein in each inhibited dilution and each substrate;

calculating the linear relationships between the reaction rates of each uninhibited protein and each concentration of the sensitivity coefficient sample at infinite inhibitor concentration; and extracting each sensitivity coefficient of each substrate for each protein from the calculated linear relationships.

2. The assay of claim 1, wherein the sensitivity coefficients are obtained from the slopes of the linear relationships.

3. The assay of claim 2, wherein the plurality of inhibited dilutions is obtained by obtaining a plurality of dilutions of at least one inhibitor which selectively inhibits a protein belonging to the plurality of proteins;

obtaining a plurality of dilutions of the sensitivity coefficient sample; and adding each dilution of the inhibitor to each dilution of the sensitivity coefficient sample.

4. The assay of claim 1, wherein the concentration or activity of more than one protein in a test sample is detected, measured or monitored.

5. The assay of claim 1, wherein the plurality of proteins comprise acetylcholinesterase and butyryicholinesterase.

6. The assay of claim 1, wherein the plurality of substrates is selected from the group consisting of acetylcholine, acetylthiocholine, hutyryicholine, butyrylthiocholine, propionyicholine, and propionyithiocholine.

7. The assay of claim 1, wherein the plurality of substrates comprise acetyithiocholine, butyrylthiolcholine, and propionylthiocholine.

8. The assay of claim 3, wherein the inhibitor is huperzine-A, tetraisopropyl pyrophosphoramide, or a combination thereof.

9. The assay of claim 1, wherein the test sample is a synthetic sample or a natural sample.

10. The assay of claim 1, wherein the natural sample is a tissue, fluid, or a membrane.

11. The assay of claim 1, wherein the sample is blood, serum, lymph, cerebrospinal fluid, breast milk, interstitial or urine.

12. The assay of claim 1, wherein the sample is diaphragm, bone marrow, brain, liver, muscle, adrenal and kidney.

13. The assay of claim 2, wherein measuring the reaction rates comprises utilizing a chromogenic substrate and measuring the absorbance of the reactions.

14. The assay of claim 5, wherein the test sample further comprises an agent which affects the concentration or activity of acetylcholinesterase, butyrylcholinesterase, or both.

15. The assay of claim 14, wherein the agent is removed from the test sample prior to measuring the reaction rates.

* * * * *

UNITED STATES PATENT AND TRADEMARK OFFICE
CERTIFICATE OF CORRECTION

| | | |
|---|---|---|
| PATENT NO. | : 6,746,850 B2 | |
| APPLICATION NO. | : 09/848370 | |
| DATED | : June 8, 2004 | |
| INVENTOR(S) | : Feaster et al. | |

It is certified that error appears in the above-identified patent and that said Letters Patent is hereby corrected as shown below:

In column 36, line 52, after "adrenal", please change "and" to --or--.

In column 36, after the last line, please add the following:

--16. A method of detecting or confirming whether a subject was exposed to an agent which affects the activity or concentration of a protein, wherein the protein belongs to a plurality of proteins and the plurality of proteins have similar or overlapping properties towards a plurality of substrates, comprising obtaining the test sample from the subject;

conducting the assay of claim 1; and comparing the activity or the concentration of the protein in the test sample with a standard.

17. The method of claim 16, wherein the protein is a cholinesterase.

18. A method of determining the identity of an agent which affects the activity or concentration of a protein, wherein the protein belongs to a plurality of proteins and the plurality of proteins have similar or overlapping properties towards a plurality of substrates, to which a subject was exposed comprising obtaining the test sample from the subject;

conducting the assay of claim 1; and comparing the activity or the concentration of the protein in the test sample with a database of activity and concentration profiles for agents which affect the concentration or activity of the protein or the plurality of proteins, or both.

UNITED STATES PATENT AND TRADEMARK OFFICE
CERTIFICATE OF CORRECTION

| | |
|---|---|
| PATENT NO. | : 6,746,850 B2 |
| APPLICATION NO. | : 09/848370 |
| DATED | : June 8, 2004 |
| INVENTOR(S) | : Feaster et al. |

It is certified that error appears in the above-identified patent and that said Letters Patent is hereby corrected as shown below:

19. The method of claim 18, wherein the protein is a cholinesterase.

20. A method of determining the efficacy or monitoring the progress of a treatment regime, wherein a subject is administered a compound which affects the activity or concentration of a protein, wherein the protein belongs to a plurality of proteins and the plurality of proteins have similar or overlapping properties towards a plurality of substrates, comprising obtaining the test sample from the subject;

conducting the assay of claim 1; and monitoring the activities or the concentrations of the protein as a function of time of the treatment regime.

21. A method of determining whether a subject suffers from a drug sensitivity or a disease which affects the activity or concentration of a protein, wherein the protein belongs to a plurality of proteins and the plurality of proteins have similar or overlapping properties towards a plurality of substrates, comprising obtaining the test sample from the subject;

conducting the assay of claim 1; and comparing the activity or the concentration of the protein in the test sample with a database of activity and concentration profiles for the protein which are typical of individuals suffering from given drug sensitivities and individuals suffering from given diseases which affect the activity or concentration of the protein, or both.

UNITED STATES PATENT AND TRADEMARK OFFICE
CERTIFICATE OF CORRECTION

| | |
|---|---|
| PATENT NO. | : 6,746,850 B2 |
| APPLICATION NO. | : 09/848370 |
| DATED | : June 8, 2004 |
| INVENTOR(S) | : Feaster et al. |

It is certified that error appears in the above-identified patent and that said Letters Patent is hereby corrected as shown below:

22. A method of measuring the concentration of red blood cells in a subject comprising obtaining the test sample from the subject;

conducting the assay of claim 5;

determining a relationship between standard concentrations of red blood cells and the activities or the concentrations of acetylcholinesterase, butyrylcholinesterase, or both; and using the relationship to calculate the concentration of red blood cells of the sample.

23. A method of screening for a candidate compound which affects the activity or concentration of a protein, wherein the protein belongs to a plurality of proteins and the plurality of proteins have similar or overlapping properties towards a plurality of substrates, comprising conducting the assay of claim 1;

contacting the candidate compound with the protein; and determining whether the concentration or activity of the protein in the test sample changes. --

Signed and Sealed this

Nineteenth Day of May, 2009

JOHN DOLL
*Acting Director of the United States Patent and Trademark Office*